(12) United States Patent
Hadley et al.

(10) Patent No.: US 11,413,263 B2
(45) Date of Patent: Aug. 16, 2022

(54) REDUCING THE RISK OF PATHOLOGICAL EFFECTS OF TRAUMATIC BRAIN INJURY

(71) Applicant: DSM IP ASSETS, B.V., Heerlen (NL)

(72) Inventors: Kevin Hadley, Elkridge, MD (US); Terence Fealey, Marietta, GA (US); Julian E. Bailes, Morgantown, WV (US)

(73) Assignee: DSM IP Assets, B.V., Heerlen (NL)

( * ) Notice: Subject to any disclaimer, the term of this patent is extended or adjusted under 35 U.S.C. 154(b) by 0 days.

(21) Appl. No.: 16/160,388

(22) Filed: Oct. 15, 2018

(65) Prior Publication Data

US 2019/0046495 A1 Feb. 14, 2019

Related U.S. Application Data

(62) Division of application No. 12/904,049, filed on Oct. 13, 2010, now abandoned.

(60) Provisional application No. 61/251,230, filed on Oct. 13, 2009.

(51) Int. Cl.
*A61K 31/232* (2006.01)
*A61K 36/02* (2006.01)

(52) U.S. Cl.
CPC ............ *A61K 31/232* (2013.01); *A61K 36/02* (2013.01)

(58) Field of Classification Search
CPC .................................................. A61K 31/232
See application file for complete search history.

(56) References Cited

U.S. PATENT DOCUMENTS

| | | | | |
|---|---|---|---|---|
| 5,506,211 A | * | 4/1996 | Barnes | A61K 31/352 514/27 |
| 6,469,049 B1 | * | 10/2002 | Meyerhoff | A61K 31/19 514/440 |
| 2002/0188997 A1 | * | 12/2002 | Lyden | A41D 13/0153 2/22 |
| 2005/0215571 A1 | * | 9/2005 | Romano | A61K 31/473 514/259.41 |
| 2006/0059605 A1 | * | 3/2006 | Ferrara | A42B 3/064 2/410 |
| 2008/0038237 A1 | * | 2/2008 | Sapolsky | A61K 38/185 424/93.21 |

FOREIGN PATENT DOCUMENTS

| | | | |
|---|---|---|---|
| JP | 2018021067 | | 2/2018 |
| WO | WO 2007/004685 | * | 1/2007 |
| WO | WO 2009/057994 | * | 5/2009 |
| WO | WO 2020/118761 | * | 10/2010 |

OTHER PUBLICATIONS

Wu et al. (Journal or Neurotrauma (2004) 21:1457-1467). (Year: 2004).*
Farooqui et al. (Journal of Neurochemistry (2007) 101:577-599) (Year: 2007).*

* cited by examiner

*Primary Examiner* — Marcos L Sznaidman
(74) *Attorney, Agent, or Firm* — Shannon McGarrah

(57) ABSTRACT

The present disclosure provides methods and compositions for reducing the risk of pathological effects of traumatic brain injury.

16 Claims, No Drawings

REDUCING THE RISK OF PATHOLOGICAL EFFECTS OF TRAUMATIC BRAIN INJURY

This application is a divisional application of U.S. application Ser. No. 12/904,049 filed Oct. 13, 2010, which claims the benefit of U.S. Provisional Application No. 61/251,230 filed Oct. 13, 2009, the entire contents of each of the which are hereby incorporated by reference.

BACKGROUND OF THE INVENTION

Field of the Invention

Traumatic brain injury (TBI) is a head injury caused by trauma to the brain. The damage can be confined to one area of the brain (focal) or involve more than one area of the brain (diffuse). TBI can be mild, moderate or severe. While some symptoms appear immediately, others do not appear until days, weeks, months or even years after the TBI event(s). Symptoms of mild TBI include headache, confusion, dizziness, blurred vision, changes in mood, and impairment in cognitive function, such as memory, learning, and attention. Symptoms of moderate to severe TBI include, in addition to those observed for mild TBI, nausea, convulsions or seizures, slurring of speech, numbness of extremities, and loss of coordination.

Background Art

Following a traumatic injury to the central nervous system (CNS), a cascade of physiological events can lead to neuronal loss including, for example, an inflammatory immune response and excitotoxicity resulting from the initial impact disrupting the glutamate, acetylcholine, cholinergic, $GABA_A$, and NMDA receptor systems. In addition, the traumatic CNS injury is frequently followed by brain edema that enhances the cascade of injury and leads to further secondary cell death and increased patient mortality.

Although major brain injury is often associated with cerebral hemorrhage or swelling, many instances have diffuse damage to neurons and their connecting fibers. Experiments employing anterograde tracers have revealed that traumatic axonal injury is a progressive event involving a focal impairment of axoplasmic transport leading to axonal swelling and ultimate disconnection in the hours to days following TBI (Raghupathi R et al., *J Neurotrauma*. 17:927-38 (2000)). Initial disruption of the axon plasma membrane results in ion channel dysregulation and loss of calcium homeostasis. Subsequently, a series of calcium dependent cascades are activated, resulting in mitochondrial damage and cytochrome c release. Ultimately, cytochrome c release may activate a caspase-3 mediated apoptotic cascade of proteolytic cleavage of cytoskeletal substrates resulting in the axonal disconnection characteristic of traumatic axonal injury (Wang et al., *Science* 284:5412 339-343 (1999); Buki et al., *J. Neurosci*. 20:2825-2834 (2000); Eldadah et al., *J. Neurotrauma*. 17:10 811-829 (2000)).

Traditional concepts of TBI also involve primary and secondary injury phases. The primary injury is represented by the moment of impact, resultant from the impartation of kinetic energy and force vectors in either a linear acceleration-deceleration or rotatory fashion, or a combination of both. In addition to the motion of the brain within the cerebrospinal fluid space, brain contact with underlying irregular surfaces of the skull, the establishing of micro-vacuum phenomena within the cerebral tissue, and the tearing and mechanical injury to neurons and particularly their projections can result in both local and remote damage. At the clinical level, treatment attempts to minimize secondary injury by preventing or treating hypotension, hypoxia, and edema.

A tertiary phase of TBI includes what are now recognized as ongoing abnormalities in glucose utilization, cellular metabolism, as well as membrane fluidity, synaptic function, and structural integrity (Hovda, *Crit Care Med*. 35:663-4 (2007); Aoyama et al, *Brain Res*. 1230:310-9 (2008), published electronically Jul. 9, 2008). In general, axon membranes are injured, ionic leakage occurs and axonal transport is interrupted in a progressive manner. This concept is reinforced by recent autopsy findings in professional contact sports athletes showing multi-focal areas of damaged neurons and their processes, remarkable for tau antibody staining, believed to represent numerous times and regions of injury from multiple concussions (Omalu et al., *Neurosurgery* 57:128-34 (2005); Omalu et al., *Neurosurgery* 59:1086-92 (2006)).

Treatment of traumatic brain injury have included diuretics, anti-convulsants, and AMPA/NMDA receptor antagonists. However, it is desirable to have treatments that can provide a prophylactic neuroprotective effect that can reduce the risk of neurological damage associated with traumatic brain injury, particularly in light of the complex physiological cascade of events that follow the initial insult in traumatic brain injury.

BRIEF SUMMARY OF THE INVENTION

The present disclosure provides a method for prophylactic treatment that reduces the risk of pathological effects associated with traumatic brain injury. In the embodiments herein, a composition comprising DHA is administered to a subject at risk for traumatic brain injury prior to the subject engaging in an activity associated with a risk of traumatic brain injury.

In some embodiments, the method comprises administering to a subject who is at risk of traumatic brain injury a composition comprising docosahexaenoate (DHA), wherein the composition is administered in a prophylactically effective amount for a sufficient time period prior to engagement in an activity associated with a risk of traumatic brain injury to reduce the risk of pathological effects of traumatic brain injury.

In some embodiments, the method for reducing the risk of pathological effects of traumatic brain injury, comprises: (a) selecting a subject who is at risk of traumatic brain injury; and (b) administering to the subject a composition comprising DHA, wherein the composition is administered in a prophylactically effective amount for a sufficient time period prior to engagement in an activity associated with a risk of traumatic brain injury to reduce the risk of pathological effects of traumatic brain injury.

In the embodiments herein, the composition comprising DHA can be any source in which DHA is present in sufficient amounts for administration to achieve a prophylactic therapeutic effect. In some embodiments, the DHA-containing composition comprises fish oil, including, among others, fish oil enriched in omega-3 fatty acids, such as oil from tuna, sardines, anchovies, and mackerel. In some embodiments, the DHA-containing composition comprises primrose oil, flaxseed oil, canola oil, walnut oil, and sunflower oil. In some embodiments, combination of oils from different sources can be used to prepare the composition. The DHA from these sources can be prepared in the form of alkylesters, triglycerides, or free fatty acids.

In some embodiments, the composition has a DHA to EPA ratio of greater than 4:1. In some embodiments, the DHA to EPA ratio is at least 10:1 or at least 100:1.

In embodiments where the DHA is in the form of an alkylester, the content of the DHA (in the form of an alkylester) is at least about 85 wt % of the total fatty acid content of the composition. In some embodiments, the alkylester composition has a DHA content of about 85 to about 96 wt % of the total fatty acid content. In some embodiments, the alkylester composition has a DHA content of about 85 to 96 wt % of the total fatty acid content, and an EPA content of about 0.1 wt % or less of the total fatty acid content.

In some embodiments of the method, the composition has a DHA content of at least about 40 wt % of the total fatty acid content. In some embodiments, the composition has a DHA content of about 40 to about 50 wt % of the total fatty acid content. In certain embodiments, the composition has a DHA content of about 40 to about 50 wt % of the total fatty acid content, and an EPA content of about 3 wt % or less, or 2 wt % or less, of the total fatty acid content. In certain embodiments, the EPA content is less than 0.2 wt % of the total fatty acid content.

In some embodiments, the composition has a DHA content of at least about 55 wt % of the total fatty acid content. In some embodiments, composition has a DHA content of about 55 to 65 wt % of the total fatty acid content. In some embodiments, the composition has a DHA content of about 55 to 65 wt % of the total fatty acid content, and an EPA content of less than 0.2 wt % of the total fatty acid content.

In some embodiments, the composition comprising the DHA is a microbial oil or derived from a microbial oil, such as from *Crypthecodinium cohnii* or *Schizochytrium* sp.

In some embodiments herein, the subject to be treated is at risk for a closed head injury, such as a concussion or contusion. A subject at risk for such injury can include, among others, a subject participating in an athletic event with occurrence of concussions. Exemplary subjects in this category include, among others, football players, boxers, and hockey players.

In some embodiments, the subject to be treated is at risk for a penetrating head injury. A subject at risk for a penetrating head injury can include, among others, a combatant in an armed conflict, for example, a soldier.

In some embodiments, a prophylactically effective amount of DHA is administered to the subject for a sufficient time period prior to an anticipated engagement in an activity associated with a risk of traumatic brain injury. In some embodiments, a prophylactically effective amount of DHA is administered for at least about 28 days prior to the anticipated engagement in the activity that is associated with a risk of traumatic brain injury. In some embodiments, a prophylactically effective amount of DHA is administered for at least about 6 weeks prior to the anticipated engagement in the activity that is associated with a risk of traumatic brain injury. In some embodiments, a prophylactically effective amount of DHA is administered for at least about two months prior to the anticipated engagement in the activity that is associated with a risk of traumatic brain injury. In some embodiments, a prophylactically effective amount of DHA is administered to the subject for at least about 6 weeks to about 6 months, at least about 2 to about 6 months, or at least about 4 months to about 6 months prior to the anticipated engagement in the activity that is associated with a risk of traumatic brain injury. In some embodiments, a prophylactically effective amount of DHA is administered to the subject for at least about 2 to about 4 months prior to the anticipated engagement in the activity that is associated with a risk of traumatic brain injury.

In the methods of the present disclosure, the subject is administered a prophylactically effective amount of DHA. In some embodiments, the DHA is administered in an amount of from about 4 mg/kg body weight/day to about 85 mg/kg body weight/day. In some embodiments, the DHA is administered in an amount of from about 4 mg/kg body weight/day to about 60 mg/kg body weight/day; from about 5 mg/kg body weight/day to about 60 mg/kg body weight/day, from about 10 mg/kg body weight/day to about 60 mg/kg body weight/day, from about 20 mg/kg body weight/day to about 60 mg/kg body weight/day; from about 10 mg/kg body weight/day to about 40 mg/kg body weight/day; or from about 20 mg/kg body weight/day to about 40 mg/kg body weight/day. In some embodiments, the DHA is administered in an amount of about 40 mg/kg body weight/day.

In some embodiments, the invention is directed to a method of protecting the brain of a human subject, the method comprising administering to the subject, before an activity associated with a potential traumatic brain injuring event, an oral dosage form comprising at least 900 mg of DHA, wherein the dosage form comprising at least about 35 wt % docosahexaenoate (DHA) of the total fatty acid content, wherein the dosage form has an eicosapentaenoate (EPA) content of less than about 2 wt % of the total fatty acid content. In some embodiments, the phrase "protecting the brain" refers to the prevention of the pathological effects of a concussion, or the reduction of the pathological effects associated with a concussion, in particular, minimizing the learning and/or memory deficits associated with traumatic brain injury, e.g., a concussion. In some embodiments, the phrase "protecting the brain" refers to an increase in brain resilience in the event of traumatic brain injury, e.g., reducing the time required after the traumatic brain injury to reduce/eliminate any learning and/or memory deficits.

In some embodiments, the activity associated with a traumatic brain injuring event is selected from the group consisting of boxing, football, soccer, or hockey, in particular events at the high school, college, or professional level. In some embodiments, the activity associated with a traumatic brain injuring event is selected from the group consisting of armed conflict or brain surgery.

In some embodiments, the invention is directed to a method of protecting the brain of a human subject, the method comprising: (1) identifying a subject at risk of experiencing a traumatic brain injuring event, and (2) administering to the subject, before an activity associated with a potential traumatic brain injuring event, an oral dosage form comprising at least 900 mg of DHA, wherein the dosage form comprises at least about 35 wt % docosahexaenoate (DHA) of the total fatty acid content, wherein the dosage form has an eicosapentaenoate (EPA) content of less than about 2 wt % of the total fatty acid content.

DETAILED DESCRIPTION OF THE INVENTION

For the descriptions herein and the appended claims, the singular forms "a", "an" and "the" include plural referents unless the context clearly indicates otherwise. Thus, for example, reference to "a compound" refers to more than one compound.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

In reference to the present disclosure, the technical and scientific terms used in the descriptions herein will have the meanings commonly understood by one of ordinary skill in the art, unless specifically defined otherwise.

Traumatic brain injury (TBI) is among the most frequently occurring and widely known events that can cause brain injury and an associated impairment of one or more neurological functions. One of the characteristics of traumatic injury is the rapid and sustained increase in polyunsaturated free fatty acids and diacylglycerols (Homayoun et al., *Neurochemical Research* 25:269-276 (2000)). In the present disclosure, a DHA-containing composition is administered to a subject prior to the traumatic brain injuring event to reduce the risk of pathological effects of traumatic brain injury.

Accordingly, in the embodiments herein, a method for reducing the risk of pathological effects of traumatic injury can comprise administering to a subject who is at risk of traumatic brain injury a composition comprising DHA, wherein the composition is administered in a prophylactically effective amount for a sufficient time period prior to engagement in an activity associated with risk of traumatic brain injury to reduce the risk of pathological effects of traumatic brain injury.

As used herein, "traumatic brain injury" or "TBI" refers to acquired brain injury or a head injury, when a trauma causes damage to the brain. The damage can be focal, i.e., confined to one area of the brain, or diffuse, involving more than one area of the brain. As used herein, "traumatic brain injury" does not include brain injury induced by ischemia/reperfusion.

In some embodiments, the subject can be at risk for a closed head injury. A "closed head injury" refers to a brain injury when the head suddenly and violently hits an object but the object does not break through the skull. In some embodiments, the closed head injury is a concussion or contusion. A concussion is a mild form of traumatic brain injury resulting in temporary impairment of neurological function which quickly resolves by itself, and where there are generally no gross structural changes to the brain as the result of the condition. An example of a subject at risk for closed head injury includes an athlete participating in a sport with occurrence of concussions, such as boxing, football, or hockey.

In some embodiments, the subject can be at risk for a penetrating head injury. A penetrating injury refers to a brain injury when an object pierces the skull and enters brain tissue. Typically, the dura mater, the outer layer of the meninges is pierced or breached by an object, such as a high velocity projectile or objects of lower velocity such as knives, or bone fragments from a skull fracture that are driven into the brain. An example of a subject at risk for traumatic brain injury from a penetrating head injury is a combatant in an armed conflict. In certain embodiments, the subject at risk for a penetrating head injury is a patient undergoing brain surgery.

A person of skill in the art can readily identify subjects at risk for traumatic brain injury and administer the compositions of DHA prophylactically to reduce the risk of pathological effects of traumatic brain injury. Thus, in some embodiments, the method for reducing the risk of pathological effects of traumatic injury can comprise: (a) selecting a subject who is at risk of traumatic brain injury; and (b) administering to the subject a composition comprising DHA, wherein the composition is administered in a prophylactically effective amount for a sufficient time period prior to engagement in an activity associated with a risk of traumatic brain injury to reduce the risk of pathological effects of traumatic brain injury.

In some embodiments, brain health can be improved after an activity known to increase the likelihood of a traumatic brain injuring event, e.g., boxing, football, soccer, hockey, armed conflict, or brain surgery, by administering the compositions of the present invention before the activity. The term brain health can refer to any known method of the maintenance or improvement of brain function by any of the standard techniques or assessments known to those of skill in the art, including those techniques and assessments provided herein.

Various pathological effects of traumatic brain injury depend on the form of the injury and its severity. In some embodiments, the pathological effects of traumatic brain injury include immediate seizures, hydrocephalus or post-traumatic ventricular enlargement, cerebral spinal fluid leaks, vascular injuries, cranial nerve injuries, and impaired cognition (thinking, memory, and reasoning), sensory processing (sight, hearing, touch, taste, and smell), communication (expression and understanding), and behavior or mental health (depression, anxiety, personality changes, aggression, acting out, and social inappropriateness).

In some embodiments, the pathological effect of traumatic brain injury is postconcussion syndrome (PCS). Symptoms of PCS include headache, dizziness, vertigo, memory problems, sleep problems, and trouble concentrating. Some patients may experience post-traumatic amnesia (PTA), either anterograde or retrograde. Anterograde PTA is impaired memory of events that happened after the traumatic brain injury, while retrograde PTA is impaired memory of events that happened before the traumatic brain injury.

Many patients with mild to moderate head injuries who experience cognitive deficits also have problems with higher level, so-called executive functions, such as planning, organizing, abstract reasoning, problem solving, and making judgments, which may make it difficult to resume pre-injury work-related activities. Some may experience aphasia, defined as difficulty with understanding and producing spoken and written language. Other pathologies affect subtle aspects of communication, such as body language and emotional, non-verbal signals. In some embodiments, the pathological effect is non-fluent aphasia, also called Broca's aphasia or motor aphasia.

Long term pathological effects of traumatic brain injury include, among others, increased incidence of Parkinson's disease and other motor problems; Alzheimer's disease; dementia pugilistica; and post-traumatic dementia. In fact, one effect of injury to neurons an increase in presence of β-amyloid precursor protein, a protein associated with Alzheimer's disease.

In some embodiments, as further discussed below, an effective amount of DHA is administered to the subject at least 6 weeks prior to the subject's anticipated engagement in an activity associated with a risk for traumatic brain injury. In some embodiments, an effective amount of DHA is administered to the subject at least 2 months prior to the subject's anticipated engagement in an activity associated with a risk for traumatic brain injury. In some embodiments, an effective amount of DHA is administered to the subject for at least about 2 months to about 6 months or more prior to the subject's anticipated engagement in the activity that is associated with a risk of traumatic brain injury. In some embodiments, an effective amount of DHA is administered to the subject for at least about 2 months to about 4 months or more prior to the subject's anticipated engagement in the activity that is associated with a risk of traumatic brain injury.

In some embodiments, the subject at risk of traumatic brain injury is administered a composition comprising docosahexaenoate or DHA. In the embodiments herein, "docosahexanoate" or refers to (all-Z)-4,7,10,13,16,19-docosahexaenoic acid, as well as any salts or derivatives thereof. Thus, the term docosahexaenoate or "DHA" encompasses the free acid DHA as well as DHA alkyl esters and triglycerides containing DHA. DHA is an ω-3 polyunsaturated fatty acid. Hence, in various embodiments, the DHA used in the method may be in the form of a phospholipid, a triglyceride, free fatty acid, and an alkyl ester. In some embodiments, the alkyl ester may comprise DHA methyl ester, ethyl ester, or propyl ester, as further described below.

In the embodiments herein, the composition comprising DHA can be any source in which DHA is present in sufficient amounts for administration to achieve the prophylactic therapeutic effect. These include, by way of example and not limitation, animal, plant and microbial sources. In some embodiments, a source of oils containing DHA suitable for the compositions and methods described herein is an animal source. Examples of animal sources include aquatic animals (e.g., fish; marine mammals; crustaceans such as krill and other euphausids; rotifers; etc.) and lipids extracted from animal tissues (e.g., brain, liver, eyes, etc.) and animal products such as eggs or milk. Examples of plant sources include macroalgae, flaxseeds, rapeseeds, corn, evening primrose, soy and borage. In some embodiments, the composition comprises fish oil, including, among others, fish oil enriched in omega-3 fatty acids, such as oil from tuna, sardines, anchovies, and mackerel. In some embodiments, the DHA-containing composition comprises primrose oil, flaxseed oil, canola oil, walnut oil, or sunflower oil. The DHA from these sources can be in the form of alkylesters, triglycerides, or free fatty acids.

In some embodiments, the DHA-containing compositions used in the methods has a DHA to eicosapentaenoate (EPA) ratio of at least 2:1 up to 4:1 wt/wt. The term "eicosapentaenoate" or "EPA" refers to eicosapentaenoic acid, known by its chemical name (all Z) 5,8,11,14,17-eicosapentaenoic acid, as well as any salts or derivatives thereof. Thus, the term "EPA" encompasses the free acid EPA as well as EPA alkyl esters and triglycerides containing EPA. EPA is also an ω-3 polyunsaturated fatty acid. Typical content of omega-3 fatty acids found in fatty fish have a ratio of DHA to EPA ratio of 4:1 or less, wt/wt. Accordingly, the DHA containing composition having a DHA to EPA ratio of at least about 2:1 up to 4:1 wt/wt can be obtained from fish oil, such as from tuna, sardines, anchovies, and mackerel, as noted above.

In some embodiments, the DHA containing composition used in the methods has a DHA to EPA ratio which is higher than 4:1 wt/wt. In some embodiments of the method, the composition of DHA has a DHA to EPA ratio which is at least 5:1 wt/wt, at least 6:1 wt/wt, 7:1 wt/wt, at least 8:1 wt/wt, at least 9:1 wt/wt, at least 10:1 wt/wt, at least 12:1 wt/wt, at least 14:1 wt/wt, at least 16:1 wt/wt, at least 18:1 wt/wt, at least 20:1 wt/wt, at least 40:1 wt/wt, at least 60:1 wt/wt, at least 80:1 wt/wt, at least 100:1 wt/wt, or higher. In some embodiments of the method, the composition of DHA has a DHA to EPA ratio of about 10:1 wt/wt, 12:1 wt/wt, 14:1 wt/wt, 16:1 wt/wt, 18:1 wt/wt, 20:1 wt/wt, 40:1 wt/wt, 60:1 wt/wt, 80:1 wt/wt, or 100:1 wt/wt.

In some embodiments, the composition of DHA is substantially free of EPA. As used herein, a composition of DHA that is "substantially free of EPA" refers to a preparation of DHA in which EPA is less than about 3 wt %, or about 2 wt %, of the total fatty acid content of the composition. Thus, in some embodiments, a composition substantially free of EPA can have less than 2 wt % of the total fatty acid content of the composition, less than 1 wt % of the total fatty acid content of the composition, less than 0.5 wt % of the total fatty acid content of the composition, less than 0.2 wt % of the total fatty acid content of the composition, or less than 0.01 wt % of the total fatty acid content of the composition. In some embodiments, the EPA is not detectable in the composition using techniques known in the art. An exemplary technique for detecting the amount of EPA is direct transmethylation of the oil to form fatty acid methyl esters (FAME) followed by separation of the products by HPLC, gas-liquid chromatography, or gas chromatography-mass spectroscopy (see, e.g., Fournier et al., *J Chromatogr A*. 1129:21-8 (2006)). In some embodiments, the DHA composition has no EPA.

DHA can also be administered substantially free of arachidonic acid (ARA). ARA refers to the compound (all-Z)-5,8,11,14-eicosatetraenoic acid (also referred to as (5Z,8Z,11Z,14Z)-icosa-5,8,11,14-tetraenoic acid), as well as any salts or derivatives thereof. Thus, the term "ARA" encompasses the free acid ARA as well as ARA alkyl esters and triglycerides containing ARA. ARA is an ω-6 polyunsaturated fatty acid. DHA is "substantially free of ARA" when ARA is less than about 3% (wt/wt) of the total fatty acid content of the dosage form. In some embodiments, ARA comprises less than about 2% (wt/wt) of the total fatty acid content of the dosage form, less than 1% (wt/wt) of the total fatty acid content of the dosage form, less than 0.5% (wt/wt) of the total fatty acid content of the dosage form, less than 0.2% (wt/wt) of the total fatty acid content of the dosage form, or less than 0.01% (wt/wt) of the total fatty acid content of the dosage form. In some embodiments, the dosage form has no detectable amount of ARA.

DHA can also be administered substantially free of docosapentaenoic acid 22:5 n-6 (DPAn-6). The term "DPAn-6" refers to docosapentaenoic acid, omega 6, known by its chemical name (all-Z)-4,7,10,13,16-docosapentaenoic acid, as well as any salts or esters thereof. The term "DPAn-6" encompasses the free acid DPAn-6 as well as DPAn-6 alkyl esters and triglycerides containing DPAn-6. DPAn-6 is an ω-6 polyunsaturated fatty acid. DHA is "substantially free of DPAn-6" when DPAn-6 is less than about 3% (wt/wt) of the total fatty acid content of the dosage form. In some embodiments, DPAn-6 comprises less than about 2% (wt/wt) of the total fatty acid content of the dosage form, less than 1% (wt/wt) of the total fatty acid content of the dosage form, less than 0.5% (wt/wt) of the total fatty acid content of the dosage form, less than 0.2% (wt/wt) of the total fatty acid content of the dosage form, or less than 0.01% (wt/wt) of the total fatty acid content of the dosage form. In some embodiments, the dosage form has no detectable amount of DPAn-6.

In some embodiments, the dosage form of the present invention does not contain a measurable amount of docosapentaenoic acid 22:5n-3 (DPAn-3); docosapentaenoic acid 22:5n-6 (DPAn-6); and/or 4,7,10,13,16,19,22,25 octacosaoctaenoic acid (C28:8).

In some embodiments, the DHA is administered in the substantial absence of therapeutic levels of albumin and its pharmaceutically acceptable salts. In some embodiments, the DHA is administered with less than 100 mg, more particularly less than 10 mg, more particularly less than 5 mg and more particularly less that 1 mg of albumin and its pharmaceutically acceptable salts. In some embodiments, the DHA is administered with no detectable amount of albumin.

In some embodiments, the composition of DHA may include an additional lipid. As used herein, the term "lipid" includes phospholipids (PL); free fatty acids; esters of fatty acids; triacylglycerols (TAG); diacylglycerides; monoacylglycerides; phosphatides; waxes (esters of alcohols and fatty acids); sterols and sterol esters; carotenoids; xanthophylls (e.g., oxycarotenoids); hydrocarbons; and other lipids known to one of ordinary skill in the art. The lipid can be chosen to have minimal adverse health effects or minimally affect the effectiveness of DHA when administered in combination with DHA.

In some embodiments, the composition of DHA may include an additional unsaturated lipid. In some embodiments, the unsaturated lipid is a polyunsaturated lipid, such as an omega-3 fatty acid or omega-6 fatty acid. An exemplary omega-6 fatty acid that may be used in the composition is docosapentaenoic acid (DPA), including DPAn-6 or DPAn-3.

In the methods and compositions herein, additional fatty acids can be present in the dosage form or unit dose or composition. These fatty acids can include fatty acids that were not removed during the purification process, i.e., fatty acids that were co-isolated with DHA from an organism. In some embodiments, one or more non-DHA fatty acids can be added to the dosage form or unit dose to achieve a desired concentration of specific non-DHA fatty acids. Any of these fatty acids can be present in various concentrations. For example, in some embodiments, the dosage form or unit dose comprises 0.01% to about 4% (wt/wt) of oleic acid. In some embodiments, the dosage form or unit dose comprises 0.01% to 0.5% (wt/wt) of one or more of the following fatty acids: (a) capric acid; (b) lauric acid; (c) myristic acid; (d) palmitic acid; (e) palmitoleic acid; (f) heptadecanoic acid; (g) stearic acid; (h) oleic acid; (i) linoleic acid; (j) α-linolenic acid; (k) arachidic acid; (l) eicosenoic acid; (m) arachidonic acid; (n) erucic acid; (o) docosapentaenoic acid 22:5n-3 (DPAn-3); and (p) nervonic acid. In some embodiments, a dosage form or unit dose comprises 0.01% to 0.1% (wt/wt) of one or more of the following fatty acids: (a) lauric acid; (b) heptadecanoic acid; (c) stearic acid; (d) arachidic acid; (e) eicosenoic acid; and (f) arachidonic acid. In some embodiments, a dosage form or unit dose comprises less than 0.5% (wt/wt) each of the following fatty acids: (a) capric acid; (b) lauric acid; (c) myristic acid; (d) palmitic acid; (e) palmitoleic acid; (f) heptadecanoic acid; (g) stearic acid; (h) linoleic acid; (i) α-linolenic acid; (j) arachidic acid; (k) eicosenoic acid; (l) arachidonic acid; (m) erucic acid; (n) docosapentaenoic acid 22:5n-3 (DPAn-3); and (o) nervonic acid. In some embodiments, the dosage form or unit doses of the present invention do not contain a measurable amount of one or more of the following fatty acids: (a) capric acid; (b) linoleic acid; (c) α-linolenic acid; and (d) docosapentaenoic acid 22:5n-3 (DPAn-3).

In some embodiments, the dosage form or unit dose comprises 0.1% to 60% (wt/wt) of one or more of the following fatty acids, or esters thereof: (a) capric acid; (b) lauric acid; (c) myristic acid; (d) palmitic acid, (e) palmitoleic acid; (f) stearic acid; (g) oleic acid; (h) linoleic acid; (i) α-linolenic acid; (j) docosapentaenoic acid 22:5n-3 (DPAn-3); (k) docosapentaenoic acid 22:5n-6 (DPAn-6); and (k) 4,7,10,13,16,19,22,25 octacosaoctaenoic acid (C28:8). In some embodiments, the dosage form or unit dose comprises 20% to 40% (wt/wt) of one or more of the following fatty acids, or esters thereof: (a) capric acid; (b) lauric acid; (c) myristic acid; (d) palmitic acid; (e) palmitoleic acid; (f) stearic acid; (g) oleic acid; (h) linoleic acid; (i) α-linolenic acid; j) docosapentaenoic acid 22:5n-3 (DPAn-3); (k) docosapentaenoic acid 22:5n-6 (DPAn-6); and (l) 4,7,10,13,16,19,22,25 octacosaoctaenoic acid (C28:8). In some embodiments, the dosage form or unit dose comprises less than 1% (wt/wt) each of the following fatty acids, or esters thereof: (a) capric acid; (b) lauric acid; (c) myristic acid; (d) palmitic acid, (e) palmitoleic acid; (f) stearic acid; (g) oleic acid; (h) linoleic acid; (i) α-linolenic acid; (j) docosapentaenoic acid 22:5n-3 (DPAn-3); (k) docosapentaenoic acid 22:5n-6 (DPAn-6); and (l) 4,7,10,13,16,19,22,25 octacosaoctaenoic acid (C28:8).

In some of embodiments of DHA dosage form described herein, the dosage form is characterized by one or more the following fatty acids (or esters thereof). The embodiments provided herein may further comprise about 2% or less (wt/wt) of capric acid (C10:0). The embodiments herein may further comprise about 6% or less (wt/wt) of lauric acid (C12:0). The embodiments herein may further comprise about 20% or less (wt/wt), or about 5% to about 20% (wt/wt) of myristic acid (C14:0). The embodiments herein may further comprise about 20% (wt/wt) or less, or about 5% to about 20% (wt/wt) of palmitic acid (C16:0). The embodiments herein may further comprise about 3% (wt/wt) or less of palmitoleic acid (C16:1n-7). The embodiments herein may further comprise about 2% (wt/wt) or less of stearic acid (C18:0). The embodiments herein may further comprise about 40% (wt/wt) or less, or about 10% to about 40% (wt/wt) of oleic acid (C18:1n-9). The embodiments herein may further comprise about 5% (wt/wt) or less of linoleic acid (C18:2). The embodiments herein may further comprise about 2% (wt/wt) or less of nervonic acid (C24:1). The embodiments herein may further comprise about 3% (wt/wt) or less of other fatty acids or esters thereof. The DHA dosage form with the preceding characteristics may comprise DHASCO®, an oil derived from *Crypthecodinium cohnii* containing docosahexaenoic acid (DHA).

An exemplary DHA (triglyceride) containing oil derived from *Crypthecodinium cohnii* is characterized by the specified amount of components listed in Table 1, where "Max" refers to the amount of the component that can be present up to the specified amount.

TABLE 1

| | Concentration (wt/wt) |
|---|---|
| Fatty Acids | |
| 10:0 | Max 2% |
| 12:0 | Max 6% |
| 14:0 | 5% to 20% |
| 16:0 | 5% to 20% |
| 16:1 | Max 3% |
| 18:0 | Max 2% |
| 18:1 | 10% to 40% |
| 18:2 | Max 5% |
| 22:6 DHA | 40% to 45% |
| 24:1 | Max 2% |
| Others | Max 3% |
| Elemental Composition | |
| Arsenic | Max 0.5 ppm |
| Copper | Max 0.1 ppm |
| Iron | Max 0.5 ppm |

TABLE 1-continued

| | Concentration (wt/wt) |
|---|---|
| Lead | Max 0.2 ppm |
| Mercury | Max 0.04 ppm |
| Phosphorous | Max 10 ppm |
| Chemical Characteristics | |
| Peroxide Value | Max 5 Meq/Kg |
| Free Fatty Acid | Max 0.4% |
| Unsaponifiable Matter | Max 3.5% |

An exemplary undiluted DHA (triglyceride) containing oil derived from *Crypthecodinium cohnii* is characterized by amount of DHA described herein, and one or more, or all of the features listed below in Table 2, where "Max" refers to the amount of the component that can be present up to the specified amount.

TABLE 2

Characteristics of Undiluted DHA Oil

| TEST | SPECIFICATION |
|---|---|
| DHA CONTENT MG/DHA/G OIL | MIN 480 MG/G |
| FREE FATTY ACID | MAX. 0.4% |
| PEROXIDE VALUE (PV) | MAX. 5 MEQ/KG |
| ANISIDINE VALUE (AV) | MAX 20 |
| MOISTURE AND VOLATILES (M & V) | MAX. 0.02% |
| UNSAPONIFIABLE MATTER | MAX. 3.5% |
| INSOLUBLE IMPURITIES | MAX. 0.1% |
| TRANS FATTY ACID | MAX. 1% |
| ARSENIC | MAX. 0.5 PPM |
| CADMIUM | MAX. 0.2 PPM |
| CHROMIUM | MAX. 0.2 PPM |
| COPPER | MAX. 0.1 PPM |
| IRON | MAX. 0.5 PPM |
| LEAD | MAX. 0.2 PPM |
| MANGANESE | MAX. 0.04 PPM |
| MERCURY | MAX. 0.04 PPM |
| MOLYBDENUM | MAX. 0.2 PPM |
| NICKEL | MAX. 0.2 PPM |
| PHOSPHORUS | MAX. 10 PPM |
| SILICON | MAX. 500 PPM |
| SULFUR | MAX. 100 PPM |
| 18:1 N-9 OLEIC ACID | MAX. 10% |
| 20:5 N-3 EPA | MAX. 0.1% |
| UNKNOWN FATTY ACIDS | MAX. 3.0% |

In some embodiments, an oil is characterized by one or more the following fatty acids (or esters thereof), expressed as wt % of the total fatty acid content. The embodiments provided herein may further comprise about 2% or less (wt/wt) of capric acid (C10:0). The embodiments provided herein may further comprise about 6% or less (wt/wt) of lauric acid (C12:0). The embodiments provided herein may further comprise about 20% or less, or about 10 to about 20% (wt/wt) of myristic acid (C14:0). The embodiments provided herein may further comprise about 15% or less, or about 5 to about 15% (wt/wt) of palmitic acid (C16:0). The embodiments provided herein may further comprise about 5% or less (wt/wt) of palmitoleic acid (C16:1n-7). The embodiments provided herein may further comprise about 2% or less (wt/wt) of stearic acid (C18:0). The embodiments provided herein may further comprise about 20% or less, or about 5% to about 20% (wt/wt) of oleic acid (C18:1n-9). The embodiments provided herein may further comprise about 2% or less (wt/wt) of linoleic acid (C18:2). The embodiments provided herein may further comprise about 2% or less (wt/wt) of nervonic acid (C24:1). The embodiments provided herein may further comprise about 3% or less (wt/wt) of other fatty acids. An oil with the preceding characteristics may be an oil derived from *Crypthecodinium cohnii* containing docosahexaenoic acid (DHA).

In some embodiments, the dosage form comprises, measured in percentage of free fatty acid, about 35-65%, 40-55%, 35-57%, or 57-65% DHA (22:6 n-3); about 0-2% capric acid (10:0); about 0-6% lauric acid (12:0); about 10-20% myristic acid (14:0); about 5-15% palmitic acid (16:0); about 0-5% palmitoleic acid (16:1); about 0-2% stearic acid (18:0); about 5-20% or 5-25% oleic acid (18:1); about 0-2% linoleic acid (18:2); and about 0-2% nervonic acid (24:1, n-9). In one embodiment, such an oil is from a microorganism of the genus *Thraustochytrium*. In another embodiment, the free fatty acid content is less than 0.4%.

The present invention also provides compositions comprising at least about 40 wt % DHA and at least about 0.1 wt % of DPAn-3. In some embodiments, the compositions comprise at least about 55, 56, 57, 58, 59, 60, 61, 62, 63, 64, 65 wt % DHA, optionally in triglyceride form, as a percentage of total fatty acids.

An exemplary DHA containing oil derived from *Crypthecodinium cohnii* is characterized by the specified amount of components listed in Table 3, where "Max" refers to the amount of the component that can be present up to the specified amount.

TABLE 3

| | CONCENTRATION (WT/WT) |
|---|---|
| FATTY ACIDS | |
| 10:0 | 0-2% |
| 12:0 | 0-6% |
| 14:0 | 10%-20% |
| 16:0 | 5%-15% |
| 16:1 | 0-5% |
| 18:0 | 0-2% |
| 18:1 | 5%-20% |
| 18:2 | 0-2%% |
| 22:6 (N-3) DHA | 57%-65% |
| 24:1 | 0-2% |
| OTHERS | 0-3% |
| ELEMENTAL COMPOSITION | |
| ARSENIC | MAX 0.5 PPM |
| COPPER | MAX 0.1 PPM |
| IRON | MAX 0.5 PPM |
| LEAD | MAX 0.2 PPM |
| MERCURY | MAX 0.2 PPM |
| PHOSPHOROUS | MAX 10 PPM |
| CHEMICAL CHARACTERISTICS | |
| PEROXIDE VALUE | MAX 5 MEQ/KG |
| FREE FATTY ACID | MAX 0.4% |
| UNSAPONIFIABLE MATTER | MAX 3.5% |
| TRANS FATTY ACIDS | <3.5% |
| MOISTURE AND VOLATILES | <0.1% |
| INSOLUBLE IMPURITIES | <0.1% |

In some embodiments, an oil is characterized by one or more the following fatty acids (or esters thereof), expressed as wt % (i.e., wt/wt) of the total fatty acid content. The embodiments provided herein may further comprise about 0.1% or less (wt/wt) of myristic acid (C14:0) or is not detectable. The embodiments provided herein may further comprise about 0.5% or less (wt/wt) of palmitic acid (C16:0). The embodiments provided herein may further comprise about 0.5% or less (wt/wt) of palmitoleic acid (C16:1n-7). The embodiments provided herein may further comprise about 0.5% or less (wt/wt) of stearic acid (C18:0), or is not detectable. The embodiments provided herein may further comprise about 4% or less (wt/wt) of oleic acid (C18:1n-9). The embodiments provided herein may further comprise less than 0.1% (wt/wt) of linoleic acid (C18:2) or is not detectable. The embodiments provided herein may further comprise less than 0.1% (wt/wt) of eicosapentaenoic acid (C20:5) or is not detectable. The embodiments provided herein may further comprise about 2% or less (wt/wt) of decosapentaenoic acid (22:5n-3). The embodiments provided herein may further comprise about 1% or less (wt/wt) of octacosaoctaenoic acid (28:8 n-3). The embodiments provided herein may further comprise about 0.5% or less (wt/wt) of tetracosaenoic acid (24:1n9). The embodiments provided herein may further comprise about 1% or less (wt/wt) of other fatty acids. The DHA in oil with the preceding characteristics may be in the form of a DHA ester, preferably an alkyl ester, such as a methyl ester, ethyl ester, propyl ester, or combinations thereof, prepared from an algal oil prepared from the *Crypthecodinium, cohnii* sp.

In some embodiments of the method, the composition used has an amount of DHA that is at least about 40 wt % of the total fatty acid content. In some embodiments, the weight % of the DHA in the composition is at least 50 wt % of the total fatty acid content, at least 55 wt % of the total fatty acid content, at least 60 wt % of the total fatty acid content; at least 70 wt % of the total fatty acid content; at least 80 wt % of the total fatty acid content; at least 85 wt % of the total fatty acid content; at least 90 wt % of the total fatty acid content; at least 95 wt % of the total fatty acid content; at least 96 wt % of the total fatty acid content; at least 97 wt % of the total fatty acid content; at least 98 wt % of the total fatty acid content; or at least 99 wt % of the total fatty acid content. As noted above, the DHA can be in the form of alkylesters, triglycerides, or free fatty acids.

In some embodiments, DHA is present in an amount of about 35% to about 99.9% (wt/wt) of the total fatty acid content of the dosage form or unit dose, about 40% to about 99% (wt/wt) of the total fatty acid content of the dosage form or unit dose, about 45% to about 98% (wt/wt) of the total fatty acid content of the dosage form or unit dose, about 65% to about 99.9% (wt/wt) of the total fatty acid content of the dosage form or unit dose, or about 85% to about 95% (wt/wt) of the total fatty acid content of the dosage form or unit dose. In some embodiments, the DHA is present in an amount greater than about 65% (wt/wt) of the total fatty acid content of the dosage form or unit dose, greater than about 85% (wt/wt) of the total fatty acid content of the dosage form or unit dose, greater than about 90% (wt/wt) of the total fatty acid content of the dosage form or unit dose, or greater than about 95% (wt/wt) of the total fatty acid content of the dosage form or unit dose. In some embodiments, the oil can be diluted with other oils, such as sunflower oil, to achieve the desired concentration of fatty acids.

In some embodiments, the DHA is about 30% (wt/wt) or more of the total fatty acid content of the dosage form or unit dose, about 30% to about 99.9% (wt/wt) of the total fatty acid content of the dosage form or unit dose, about 35% to about 99.9% (wt/wt) of the total fatty acid content of the dosage form or unit dose, about 35% to about 60% (wt/wt) of the total fatty acid content of the dosage form or unit dose, about 35% to about 50% (wt/wt) of the total fatty acid content of the dosage form or unit dose, about 37% to about 45% (wt/wt) of the total fatty acid content of the dosage form or unit dose, or about 38% to about 43% (wt/wt) of the total fatty acid content of the dosage form or unit dose. In some embodiments, the DHA is greater than about 35%, about 37%, about 38%, about 39% or about 40% (wt/wt) of the total fatty acid content of the dosage form or unit dose. In some embodiments, the DHA is about 30% to about 99.5% (wt/wt) of the total fatty acid content of the dosage form or unit dose, or about 40% to about 65% (wt/wt) of the total fatty acid content of the dosage form or unit dose.

In some of these embodiments, the DHA comprises about 40% to about 45% (wt/wt) of the total fatty acid content of the dosage form or unit dose. In some of these embodiments, the DHA comprises about 35% to about 45% (wt/wt) of the total fatty acid content of the dosage form or unit dose. In some of embodiments, the DHA comprises about 55% to about 67% (wt/wt) of the total fatty acid content of the dosage form or unit dose. In some embodiments, the DHA comprises greater than about 70% (wt/wt) of the total fatty acid content of the dosage form or unit dose. In some embodiments, the DHA comprises about 85% to about 99.5% (wt/wt) of the total fatty acid content of the dosage form or unit dose.

In some embodiments, the DHA is greater than about 80% (wt/wt) of the total oil content of the dosage form or unit dose, about 80% to 99.9% (wt/wt) of the total oil content of the dosage form or unit dose, about 85% to about 99% (wt/wt) of the total oil content of the dosage form or unit dose, about 87% to about 98% (wt/wt) of the total oil content of the dosage form or unit dose, or about 90% to about 97% (wt/wt) of the total oil content of the dosage form or unit dose. In some embodiments, the DHA is greater than about 95%, about 97%, about 98%, about 99% or about 99.5% (wt/wt) of the total oil content of the dosage form or unit dose. With respect to comparison of DHA to total fatty acid content or total oil content, weight % can be determined by calculating the area under the curve (AUC) using standard means, e.g., dividing the DHA AUC by the total fatty acid AUC.

As used herein, "or less" or "less than about" refers to percentages that include 0%, or amounts not detectable by current means. As used herein, "max" refers to percentages that include 0%, or amounts not detectable by current means.

In some embodiments, the DHA is greater than about 80% (wt/wt) of the total fatty acid content of the dosage form or unit dose, about 80% to 99.9% (wt/wt) of the total fatty acid content of the dosage form or unit dose, about 85% to about 99% (wt/wt) of the total fatty acid content of the dosage form or unit dose, about 87% to about 98% (wt/wt) of the total fatty acid content of the dosage form or unit dose, or about 90% to about 97% (wt/wt) of the total fatty acid content of the dosage form or unit dose. In some embodiments, the DHA is great than about 95%, about 97%, about 98%, about 99% or about 99.5% (wt/wt) of the total fatty acid content of the dosage form or unit dose.

In some embodiments, the DHA comprises about 35% to about 96% of the weight of the dosage form or unit dose. In some embodiments, the DHA comprises about 38% to about 42% of the weight of the dosage form or unit dose. In some embodiments, the DHA in the dosage form or unit dose comprises about 35% to about 45% of the total weight of the dosage form or unit dose. In some embodiments, the DHA in the dosage form or unit dose comprises about 55% of the total weight of the dosage form or unit dose. In some embodiments, the DHA in the dosage form or unit dose comprises about 85% to about 96% of the total weight of the dosage form or unit dose.

In some embodiments, the DHA is about 30% (wt/wt) or more of the total oil content of the dosage form or unit dose, about 30% to about 99.9% (wt/wt) of the total oil content of the dosage form or unit dose, about 35% to about 99.9% (wt/wt) of the total oil content of the dosage form or unit dose, about 35% to about 60% (wt/wt) of the total oil content of the dosage form or unit dose, about 35% to about 50%

(wt/wt) of the total oil content of the dosage form or unit dose, about 37% to about 45% (wt/wt) of the total oil content of the dosage form or unit dose, or about 38% to about 43% (wt/wt) of the total oil content of the dosage form or unit dose. In some embodiments, the DHA is greater than about 35%, about 37%, about 38%, about 39% or about 40% (wt/wt) of the total oil content of the dosage form or unit dose. In some embodiments, the DHA is about 30% to about 99.5% (wt/wt) of the total oil content of the dosage form or unit dose, or about 40% to about 65% (wt/wt) of the total oil content of the dosage form or unit dose.

In some embodiments, the composition has a DHA content of about 40 to about 50 wt % of the total fatty acid content. In some embodiments, the composition has a DHA content of about 40 to about 50 wt % of the total fatty acid content, and an EPA content of about 3 wt % or less, or 2 wt % or less, of the total fatty acid content. In some embodiments, the composition has a DHA content of about 40 to 50 wt % of the total fatty acid content, and an EPA content of less than 0.2 wt % of the total fatty acid content. In some embodiments, the composition has a DHA content of about 55 to 60 wt % of the total fatty acid content. In some embodiments, the composition has a DHA content of about 55 to 60 wt % of the total fatty acid content and an EPA content of less than about 0.2 wt % of the total fatty acid content. In some of these embodiments, the DHA is in the form of a triglyceride.

In the embodiments described herein, the composition of DHA having a ratio of DHA to EPA greater than 4:1 wt/wt can be obtained by standard techniques known in the art. In some embodiments, EPA may be removed during the purification of DHA, or alternatively, the DHA may be from an organism that produces DHA with the levels of EPA described herein, for example a production organism is selected that produces DHA with an insubstantial amount of EPA. DHA can be purified to various levels. DHA purification can be achieved by any means known to those of skill in the art, and can include the extraction of total oil from an organism which produces DHA. In some embodiments, EPA, ARA, and/or DPAn-6 are then removed from the total oil, for example, via chromatographic methods. Alternatively, DHA purification can be achieved by extraction of total oil from an organism which produces DHA, but produces little, if any, amount of EPA, ARA, DPAn-6, and/or flavonoids. In some embodiments, the oil can be diluted with other oils, such as sunflower oil to achieve the desired concentration of fatty acids.

Microbial oils useful in the present invention can be recovered from microbial sources by any suitable means known to those in the art. For example, the oils can be recovered by extraction with solvents such as chloroform, hexane, methylene chloride, methanol and the like, or by supercritical fluid extraction. Alternatively, the oils can be extracted using extraction techniques, such as are described in U.S. Pat. No. 6,750,048 and International Pub. No. WO 2001/053512, both filed Jan. 19, 2001, and entitled "Solventless extraction process," both of which are incorporated herein by reference in their entirety. Processes for the preparation of various forms of DHA are also described in, among others, U.S. Pub. No. 2009/0023808 "Production and Purification of Esters of Polyunsaturated Fatty Acids" by Raman et al., and U.S. Pub. No. 2007/0032548 "Polyunsaturated fatty acids for treatment of dementia and pre-dementia-related conditions" by Ellis, incorporated herein by reference.

Additional extraction and/or purification techniques are taught in International Pub. No. WO 2001/076715; International Pub. No. WO 2001/076385; U.S. Pub. No. 2007/0004678; U.S. Pub. No. 2005/0129739; U.S. Pat. No. 6,399,803; and International Pub. No. WO 2001/051598; all of which are incorporated herein by reference in their entirety. The extracted oils can be evaporated under reduced pressure to produce a sample of concentrated oil material. Processes for the enzyme treatment of biomass for the recovery of lipids are disclosed in International Pub. No. WO 2003/092628; U.S. Pub. No. 2005/0170479; EP Pat. Pub. 0776356 and U.S. Pat. No. 5,928,696, the last two entitled "Process for extracting native products which are not water-soluble from native substance mixtures by centrifugal force," all of which are incorporated herein by reference in their entirety.

In some embodiments, the DHA can be prepared as esters using a method comprising: a) reacting a composition comprising polyunsaturated fatty acids in the presence of an alcohol and a base to produce an ester of a polyunsaturated fatty acid from the triglycerides; and b) distilling the composition to recover a fraction comprising the ester of the polyunsaturated fatty acid, optionally wherein the method further comprises: c) combining the fraction comprising the ester of the polyunsaturated fatty acid with urea in a medium; d) cooling or concentrating the medium to form a urea-containing precipitate and a liquid fraction; and e) separating the precipitate from the liquid fraction. See, e.g., U.S. Pub. No. 2009/0023808, incorporated by reference herein in its entirety. In some embodiments, the purification process includes starting with refined, bleached, and deodorized oil (RBD oil), then performing low temperature fractionation using acetone to provide a concentrate. The concentrate can be obtained by base-catalyzed transesterification, distillation, and silica refining to produce the final DHA product.

Methods of determining purity levels of fatty acids are known in the art, and may include, e.g., chromatographic methods such as, e.g., HPLC silver ion chromatographic columns. Alternatively, purity levels may be determined by gas chromatography, with or without converting DHA to the corresponding alkyl ester. The percentage of fatty acids may also be determined using Fatty Acid Methyl Ester (FAME) analysis.

In some embodiments, the DHA esters can be derived from undiluted oil from a single cell microorganism, and in some embodiments, from undiluted DHASCO-T® (Martek Biosciences Corporation, Columbia, Md.). In some embodiments, the oil from which DHA compositions can be derived includes single cell microorganism oils that are manufactured by a controlled fermentation process followed by oil extraction and purification using methods common to the vegetable oil industry. In certain embodiments, the oil extraction and purification steps can include refining, bleaching, and deodorizing. In some embodiments, the undiluted DHA oil comprises about 40% to about 50% DHA by weight (about 400-500 mg DHA/g oil). In certain embodiments, the undiluted DHA oil can be enriched by cold fractionation (resulting in oil containing about 60% wt/wt of DHA triglyceride), which DHA fraction optionally can be transesterified, and subjected to further downstream processing to produce the active DHA of the invention. In some embodiments of the invention, downstream processing of the oil comprises distillation and/or silica refinement.

Thus, to produce oil from which DHA can be derived, in certain aspects, the following steps can be used: fermentation of a DHA producing microorganism; harvesting the biomass; spray drying the biomass; extracting oil from the biomass; refining the oil; bleaching the oil; chill filtering the oil; deodorizing the oil; and adding an antioxidant to the oil.

In some embodiments, the microorganism culture can be progressively transferred from smaller scale fermenters to a production size fermenter. In some embodiments, following a controlled growth over a pre-established period, the culture can be harvested by centrifugation then pasteurized and spray dried. In certain embodiments, the dried biomass can be flushed with nitrogen and packaged before being stored frozen at −20. C. In certain embodiments, the DHA oil can be extracted from the dried biomass by mixing the biomass with n-hexane or isohexane in a batch process which disrupts the cells and allows the oil and cellular debris to be separated. In certain embodiments, the solvent can then be removed.

In some embodiments, the crude DHA oil can then undergo a refining process to remove free fatty acids and phospholipids. The refined DHA oil can be transferred to a vacuum bleaching vessel to assist in removing any remaining polar compounds and pro-oxidant metals, and to break down lipid oxidation products. The refined and bleached DHA oil can undergo a final clarification step by chilling and filtering the oil to facilitate the removal of any remaining insoluble fats, waxes, and solids.

Optionally, the DHA can be deodorized under vacuum in a packed column, counter current steam stripping deodorizer. Antioxidants such as ascorbyl palmitate, alpha-tocopherol, and tocotrienols can optionally be added to the deodorized oil to help stabilize the oil. In some embodiments, the final, undiluted DHA oil is maintained frozen at −20° C. until further processing.

In some embodiments, the DHA oil can be converted to DHA ester by methods known in the art. In some embodiments, DHA esters of the invention can be produced from DHA oil by the following steps: cold fractionation and filtration of the DHA oil (to yield for example about 60% triglyceride oil); direct transesterification (to yield about 60% DHA ethyl ester); molecular distillation (to yield about 88% DHA ethyl ester); silica refinement (to yield about 90% DHA ethyl ester); and addition of an antioxidant.

In some embodiments, the cold fractionation step can be carried out as follows: undiluted DHA oil (triglyceride) at about 500 mg/g DHA is mixed with acetone and cooled at a controlled rate in a tank with −80° C. chilling capabilities. Saturated triglycerides crystallize out of solution, while polyunsaturated triglycerides at about 600 mg/g DHA remain in the liquid state. The solids containing about 300 mg/g can be filtered out with a 20 micron stainless steel screen from the liquid stream containing about 600 mg/g DHA. The solids stream can then be heated (melted) and collected. The 600 mg/g DHA liquid stream can be desolventized with heat and vacuum and then transferred to the transesterification reactor.

In some embodiments, the transesterification step is carried out on the 600 mg/g DHA oil, wherein the transesterification is done via direct transesterification using ethanol and sodium ethoxide. The transesterified material (DHA-ethyl ester) can then be subject to molecular distillation and thus, further distilled (3 passes, heavies, lights, heavies) to remove most of the other saturated fatty acids and some sterols and non-saponifiable material. The DHA-ethyl ester (DHA-EE) can be further refined by passing it through a silica column.

DHA free fatty acids (DHA-FFA) can be made using, for example, the DHA containing oils described above. In some embodiments, the DHA-FFA can be obtained from DHA esters. DHA triglycerides, for example, can be saponified followed by a urea adduction step to make free fatty acids.

Any source of DHA can be used in the compositions and methods described herein, including, for example, animal, plant and microbial sources. Examples of animal sources include aquatic animals (e.g., fish, marine mammals, crustaceans, rotifers, etc.) and lipids extracted from animal tissues (e.g., brain, liver, eyes, etc.). Examples of plant sources include macroalgae, flaxseeds, rapeseeds, corn, evening primrose, soy and borage. Examples of microorganisms include microalgae, protists, bacteria and fungi (including yeast). For example, the DHA may be purified from fish oil, plant oil, seed oil, or other naturally occurring oils such that the DHA to EPA ratio are within the scope described herein. In some embodiments, the source of DHA may be a genetically modified plant or a genetically modified microorganism manipulated to produce DHA.

In some embodiments, the composition of DHA is a microbial oil or is derived from a microbial oil. "Microbial oil" refers to those oils naturally produced by microorganisms. "Derived from" refers to a modification of the microbial oil, such as esters prepared from the microbial oil; isolated or purified components of the microbial oil; or other processing of the microbial oil, such as concentration of the oil, to alter the percent weight of a component of the microbial oil. Exemplary microbes from which microbial oil may be obtained, include, among others, the microbial groups Stramenopiles, Thraustochytrids, and Labrinthulids. Stramenopiles includes microalgae and algae-like microorganisms, including the following groups of microorganisms: Hamatores, Proteromonads, Opalines, Develpayella, Diplophrys, Labrinthulids, Thraustochytrids, Biosecids, Oomycetes, Hypochytridiomycetes, Commation, Reticulosphaera, Pelagomonas, Pelagococcus, Ollicola, Aureococcus, Parmales, Diatoms, Xanthophytes, Phaeophytes (brown algae), Eustigmatophytes, Raphidophytes, Synurids, Axodines (including Rhizochromulinaales, Pedinellales, Dictyochales), Chrysomeridales, Sarcinochrysidales, Hydrurales, Hibberdiales, and Chromulinales. The Thraustochytrids include the genera *Schizochytrium* (species include *aggregatum, limnaceum, mangrovei, minutum, octosporum*), *Thraustochytrium* (species include *arudimentale, aureum, benthicola, globosum, kinnei, motivum, multirudimentale, pachydermum, proliferum, roseum, striatum*), *Ulkenia* (species include *amoeboidea, kerguelensis, minuta, profunda, radiate, sailens, sarkariana, schizochytrops, visurgensis, yorkensis*), *Aplanochytrium* (species include *haliotidis, kerguelensis, profunda, stocchinoi*), *Japonochytrium* (species include *marinum*), *Althornia* (species include *crouchii*), and *Elina* (species include *marisalba, sinorifica*). The Labrinthulids include the genera *Labyrinthula* (species include *algeriensis, coenocystis, chattonii, macrocystis, macrocystis atlantica, macrocystis macrocystis, marina, minuta, roscofensis, valkanovii, vitellina, vitellina pacifica, vitellina vitellina, zopfi*), *Labyrinthomyxa* (species include *marina*), *Labyrinthuloides* (species include *haliotidis, yorkensis*), *Diplophrys* (species include *archeri*), *Pyrrhosorus\** (species include *marinus*), *Sorodiplophrys\** (species include *stercorea*), and *Chlamydomyxa\** (species include *labyrinthuloides, montana*) (\*=there is no current general consensus on the exact taxonomic placement of these genera).

In some embodiments, the microbial oil source is oleaginous microorganisms, such as certain marine algae. As used herein, "oleaginous microorganisms" are defined as microorganisms capable of accumulating greater than 20% of the dry weight of their cells in the form of lipids. In some embodiments, the DHA is obtained or derived from a phototrophic or heterotrophic single cell organism or multicellular organism, e.g., an algae. Thus, in some embodiments, the microbial oil is an algal oil. For example, the DHA may be obtained or derived from a diatom, e.g., a marine dinoflagellates (algae), such as *Crypthecodinium* sp., *Thraustochytrium* sp., *Schizochytrium* sp., or combinations thereof. Exemplary samples of *C. cohnii*, have been deposited with the American Type Culture Collection at Rockville, Md., and assigned the accession numbers 40750, 30021, 30334-30348, 3054130543, 30555-30557, 30571, 30572, 30772-30775, 30812, 40750, 50050-50060, and 50297-50300.

As used herein, the term microorganism, or any specific type of organism, includes wild strains, mutants or recombinant types. Organisms which can produce an enhanced level of oil containing DHA are considered to be within the scope of this invention. For example, cultivation of dinoflagellates such as *C. cohnii* has been described previously. See, e.g., U.S. Pat. No. 5,492,938 and Henderson et al., *Phytochemistry* 27:1679-1683 (1988). Also included are microorganisms designed to efficiently use more cost-effective substrates while producing the same amount of DHA as the comparable wild-type strains.

Organisms useful in the production of DHA can also include any manner of transgenic or other genetically modified organisms, such as a genetically modified plant or a genetically modified microorganism manipulated to produce DHA. e.g., plants, grown either in culture fermentation or in crop plants, e.g., cereals such as maize, barley, wheat, rice, sorghum, pearl millet, corn, rye and oats; or beans, soybeans, peppers, lettuce, peas, *Brassica* species (e.g., cabbage, broccoli, cauliflower, brussel sprouts, rapeseed, and radish), carrot, beets, eggplant, spinach, cucumber, squash, melons, cantaloupe, sunflowers, safflower, canola, flax, peanut, mustard, rapeseed, chickpea, lentil, white clover, olive, palm, borage, evening primrose, linseed, and tobacco. In some embodiments, the DHA is derived from a soybean source, including wild type and genetically modified soybean sources.

In some embodiments, the DHA may be purified in the form of free fatty acids, fatty acid esters, phospholipids, triglycerides, diglycerides, monoglycerides or combinations thereof by any means known to those of skill in the art. In some embodiments, the DHA comprises an ester. The term "ester" refers to the replacement of the hydrogen in the carboxylic acid group of the DHA molecule with another substituent. Typical esters are known to those in the art, a discussion of which is provided by Higuchi, T. and V. Stella in "Pro-drugs as Novel Delivery Systems," Vol. 14, A.C.S. Symposium Series, Bioreversible Carriers in Drug Design, Ed. Edward B. Roche, American Pharmaceutical Association, Pergamon Press (1987), and Protective Groups in Organic Chemistry, McOmie ed., Plenum Press, New York (1973). In some embodiments, the ester is an alkyl ester. Examples of more common esters include C1-C6 esters, e.g., methyl, ethyl, propyl, butyl, pentyl, hexyl, or branched variations thereof, e.g., isopropyl, isobutyl, isopentyl, or t-butyl. In some embodiments, the ester is a carboxylic acid protective ester group, esters with aralkyl (e.g., benzyl, phenethyl), esters with lower alkenyl (e.g., allyl, 2-butenyl), esters with lower-alkoxy-lower-alkyl (e.g., methoxymethyl, 2-methoxyethyl, 2-ethoxyethyl), esters with lower-alkanoyloxy-lower-alkyl (e.g., acetoxymethyl, pivaloyloxymethyl, 1-pivaloyloxyethyl), esters with lower-alkoxycarbonyl-lower-alkyl (e.g., methoxycarbonylmethyl, isopropoxycarbonylmethyl), esters with carboxy-lower alkyl (e.g., carboxymethyl), esters with lower-alkoxycarbonyloxy-lower-alkyl (e.g., 1-(ethoxycarbonyloxy)ethyl, 1-(cyclohexyloxycarbonyloxy)ethyl), esters with carbamoyloxy-lower alkyl (e.g., carbamoyloxymethyl), and the like. In some embodiments, the added substituent is a cyclic hydrocarbon group, e.g., C1-C6 cycloalkyl, or C1-C6 aryl ester. Other esters include nitrobenzyl, methoxybenzyl, benzhydryl, and trichloroethyl. In some embodiments, the ester substituent is added to a DHA free acid molecule when the DHA is in a purified or semi-purified state. Alternatively, the DHA ester is formed upon conversion of a triglyceride to a ester. One of skill in the art can appreciate that some non-esterified DHA molecules can be present in the DHA compositions, e.g., DHA molecules that have not been esterified, or DHA triglyceride ester linkages that have been cleaved, e.g., hydrolyzed. In some embodiments, the non-esterified DHA molecules or the DHA triglyceride molecules constitute less than 3% (mol/mol), about 0.01% to about 2% (mol/mol), about 0.05% to about 1% (mol/mol), or about 0.01% to about 0.5% (mol/mol) of the total DHA molecules. In some embodiments, the amount of ethyl ester of DHA in the compositions may be at least about 91, 92, 93, 94, 95, 96, 97, 98, or 99 wt %.

In some embodiments, the DHA of the present invention is a triglyceride, diglyceride or monoglyceride. A "triglyceride" is a glyceride in which the glycerol is esterified with three fatty acid groups. Typical triglycerides are known to those in the art. In some embodiments, the DHA is in the form of a triglyceride or a diglyceride, wherein one or more fatty acid groups other than DHA are present in the triglyceride or diglyceride. In some embodiments, DHA is the only fatty acid group on a triglyceride or diglyceride molecule. In some embodiments, one or more fatty acid groups of a triglyceride have been hydrolyzed, or cleaved.

In some embodiments, the DHA of the present invention is in the form of free fatty acid. "Free fatty acid" refers to fatty acid compounds in their acidic state, and salt derivatives thereof.

In some embodiments, the DHA may be purified in the form of free fatty acids, fatty acid esters, phospholipids, or triglycerides by any means known to those of skill in the art. Processes for the preparation of various forms of DHA are described in, among others, U.S. Pub. No. 2009/0023808 "Production and Purification of Esters of Polyunsaturated Fatty Acids" by Raman et al. and U.S. Pub. No. 2007/0032548 "Polyunsaturated fatty acids for treatment of dementia and pre-dementia-related conditions" by Ellis, incorporated herein by reference. As used herein, "ester" refers to a molecule wherein the hydrogen in the carboxylic acid group of the DHA molecule has been replaced with another substituent. Examples of common esters include methyl, ethyl, propyl, butyl, pentyl, t-butyl, benzyl, nitrobenzyl, methoxybenzyl, benzhydryl, and trichloroethyl. In some embodiments, the ester is an alkyl ester, e.g., a methyl ester, ethyl ester or propyl ester. In some embodiments, the ester substituent is added to the DHA free acid molecule when the DHA is in a purified or semi-purified state. Alternatively, the DHA ester is formed upon conversion of a triglyceride to a ester. In some embodiments, the amount of alkyl ester of DHA in the compositions can be at least about 80, 85, 86, 87, 88, 89, 90, 91, 92, 93, 94, 95, 96, 97, 98, or 99 wt %. In some embodiments, DHA alkyl ester is at least about 85 wt % of the total fatty acid content of the composition. In certain embodiments, the DHA alkylester is about 85 to 96 wt % of the total fatty acid content. In some embodiments, the composition has a DHA alkyl ester content of about 85 to 96 wt % of the total fatty acid content, and an EPA content of about 0.1 wt % or less of the total fatty acid content. In certain embodiments, the DHA alkyl ester is an ethyl ester. One of skill in the art can appreciate that some non-esterified DHA molecules may be present in the composition, e.g., DHA molecules that have not been esterified, or DHA ester linkages that have been cleaved, e.g., hydrolyzed. In some embodiments, the nonesterified DHA molecules constitute less than 3% (mol/mol), about 2% to about 0.01% (mol/mol), about 1% to about 0.05% (mol/mol), or about 5% to about 0.1% (mol/mol) of the total DHA molecules. Alternatively, in some embodiments, the DHA may be purified in the free acid form or in a salt form.

An exemplary method for producing a DHA ester may comprise: a) reacting the composition comprising DHA in the presence of an alcohol and a base to produce an ester of a polyunsaturated fatty acid from the DHA in triglycerides; and b) distilling the composition to recover a fraction comprising the ester of the polyunsaturated fatty acid, optionally wherein the method further comprises: c) combining the fraction comprising the ester of the polyunsaturated fatty acid with urea in a medium; d) cooling or concentrating the medium to form a urea-containing precipitate and a liquid fraction; and e) separating the precipitate from the liquid fraction. In some embodiments, the purification process includes starting with refined, bleached, and deodorized oil (RBD oil), then performing low temperature fractionation using acetone to provide a concentrate. See U.S. application Ser. No. 12/163,555, incorporated herein by reference. The concentrate may be obtained by base-catalyzed transesterification, distillation, and silica refining to produce a DHA product.

As noted above, methods of determining purity levels of fatty acids are known in the art, and may include, e.g., chromatographic methods such as, e.g., HPLC silver ion chromatographic columns. Alternatively, purity levels may be determined by gas chromatography, with or without converting DHA to the corresponding alkyl ester. The percentage of fatty acids may also be determined using Fatty Acid Methyl Ester (FAME) analysis.

In some embodiments, the composition of DHA may include an additional lipid. As used herein, the term "lipid" includes phospholipids (PL); free fatty acids; esters of fatty acids; triacylglycerols (TAG); diacylglycerides; monoacylglycerides; phosphatides; waxes (esters of alcohols and fatty acids); sterols and sterol esters; carotenoids; xanthophylls (e.g., oxycarotenoids); hydrocarbons; and other lipids known to one of ordinary skill in the art. The lipid can be chosen to have minimal adverse health effects or minimally affect the effectiveness of DHA when administered in combination with DHA.

In some embodiments, the composition of DHA may include an additional unsaturated lipid. In some embodiments, the unsaturated lipid is a polyunsaturated lipid, such as another omega-3 fatty acid or an omega-6 fatty acid. An exemplary omega-6 fatty acid that may be used in the composition is docosapentaenoic acid (DPA), including DPAn-6 or DPAn-3.

In some embodiments the dosage form comprises 0.1% to 20% of one or more of the following fatty acids: (a) capric acid; (b) lauric acid; (c) myristic acid; (d) palmitic acid; (e) palmitoleic acid; (f) stearic acid; (g) oleic acid; (h) linoleic acid; (i) α-linolenic acid; j) DPA n-3 (22:5, n-3); (k) DPA n-6 (22:5, n-6); and (l) 4,7,10,13,16,19,22,25 octacosaoctaenoic acid (C28:8). In some embodiments, the dosage form comprises 1% to 5% of one or more of the following fatty acids: (a) capric acid; (b) lauric acid; (c) myristic acid; (d) palmitic acid; (e) palmitoleic acid; (f) stearic acid; (g) oleic acid; (h) linoleic acid; (i) α-linolenic acid; (j) DPA n-3 (22:5, n-3); (k) DPA n-6 (22:5, n-6); and (l) 4,7,10,13,16,19,22,25 octacosaoctaenoic acid (C28:8). In some embodiments, the dosage form comprises less than 1% each of the following fatty acids: (a) capric acid; (b) lauric acid; (c) myristic acid; (d) palmitic acid; (e) palmitoleic acid; (f) stearic acid; (g) oleic acid; (h) linoleic acid; (i) α-linolenic acid; (j) docosapentaenoic acid 22:5n-3, 22:5w3 (DPAn-3); (k) docosapentaenoic acid 22:5n-6, 22:5w6 (DPAn-6); and (l) 4,7,10,13, 16,19,22,25 octacosaoctaenoic acid (C28:8).

In some embodiments, the DHA composition may comprise DHASCO®. DHASCO® is an oil derived from $Crypthecodinium\ cohnii$ containing high amounts of docosahexaenoic acid (DHA), and more specifically contains the following approximate exemplary amounts of these fatty acids, as a percentage of the total fatty acids: myristic acid (14:0) 10-20%; palmitic acid (16:0) 10-20%; palmitoleic acid (16:1) 0-2%; stearic acid (18:0) 0-2%; oleic acid (18:1) 10-30%; linoleic acid (18:2) 0-5%; arachidic acid (20:0) 0-1%; behenic acid (22:0) 0-1%; docosapentaenoic acid (22:5) 0-1%; docosahexanoic acid (22:6) (DHA) 40-45%; nervonic acid (24:1) 0-2%; and others 0-3%. The composition of DHASCO is also described in U.S. Pat. No. 5,397, 591 by Kyle et al., U.S. Pat. No. 5,407,957 by Kyle et al., U.S. Pat. No. 5,492,938 by Kyle et al., and U.S. Pat. No. 5,711,983 by Kyle et al.; the references of which are incorporated herein by reference. As will be understood by the skilled artisan, the content of various components may vary because of variations on the manufacturing processes, with variations of DHA content being about 40 to 50 wt % of the total fatty acid content. In some embodiments, the DPAn-6 to EPA ratio is about 6:1 to about 7:1 wt/wt, and the DHA to DPAn-6 ratio is about 2:1 to about 3:1 wt/wt.

Alternatively, in some embodiments, the DHA composition may comprise Life's DHA™ (also formerly referenced as DHA™-S and DHASCO®-S), an oil derived from the Thraustochytrid, $Schizochytrium$ sp., that contains a high amount of DHA and also contains docosapentaenoic acid (n-6) (DPAn-6). More specifically, DHA™-S contains the following approximate exemplary amounts of these fatty acids, as a percentage of total fatty acids: myristic acid (14:0) 8.71%; palmitic acid (16:0) 22.15%; stearic acid (18:0) 0.66%; linoleic acid (18:2) 0.46%; arachidonic acid (20:4) 0.52%; eicosapentenoic acid (20:5, n-3) 1.36%; docosapentaenoic acid (22:5, n-6) (DPAn-6) 16.28%; docosahexaenoic acid (DHA) (22:6, n-3) 41.14%; and others 8%. The characteristics of DHASCO®-S are also described in Ryan et al., $Amer.\ J.\ Therapeutics$ 16:183-192 (2009), incorporated herein by reference. As will be understood by the skilled artisan, the content of various components may vary because of variations on the manufacturing processes, with variations of DHA content being about 40 to 50 wt % of the total fatty acid content. DHA alkylesters are also described in U.S. application Ser. No. 12/572,263, filed Oct. 1, 2009, incorporated herein by reference. DHA alkylesters can be prepared by techniques known in the art, such as U.S. Pat. No. 6,395,778, incorporated herein by reference.

In some embodiments, the composition comprises DHA in the form of an ethyl ester derived from $Crypthecodinium\ cohnii$, with the ester being about 89 wt % of the total fatty acid content of the composition. More specifically, the compositions contain the following exemplary amounts of the following fatty acid esters (i.e., ethyl esters) by weight: docosahexaenoic acid (22:6 w3) 89%; myristic acid (14:0) 0.1%; palmitic acid (16:0) 0.48%; palmitoleic acid (16:1 w7) 0.39%; oleic acid (18:1 w9) 3.9%; docosapentaenoic acid (22:5 w3) 1.26%; octacosaoctaenoic acid (28:8 w3) 0.87%; tetracosaenoic acid (24:1 w9) 0.29%; and others 4.87%. EPA is not detectable by known methods of measuring EPA. As will be understood by the skilled artisan, the content of various components may vary because of variations on the manufacturing processes, with variations of DHA ethyl ester content being 85 to 96 wt % of the total fatty acid content.

In some embodiments, the dosage form comprises, measured in weight percent of the total free fatty acid content, about 35-65%, 40-55%, 35-57%, or 57-65% DHA (22:6 n-3); about 0-2% capric acid (10:0); about 0-6% lauric acid (12:0); about 10-20% myristic acid (14:0); about 5-15% palmitic acid (16:0); about 0-5% palmitoleic acid (16:1); about 0-2% stearic acid (18:0); about 5-20% or 5-25% oleic acid (18:1); about 0-2% linoleic acid (18:2); and about 0-2% nervonic acid (24:1n-9). In certain embodiments, such an oil is from a microorganism of the genus *Thraustochytrium*. In other embodiments, the free fatty acid content is less than 0.4%. In some embodiments, the dosage form comprises, measured in weight percent of total free fatty acid content, about 35-45% DHA (22:6n-3); about 0-2% lauric acid (12:0); about 5-10% myristic acid (14:0); about 5-20% palmitic acid (16:0); about 0-5% palmitoleic acid (16:1); about 0-5% stearic acid (18:0); about 0-5% vaccenic acid or oleic acid (18:1 n-7 and n-9, respectively); about 0-2% linoleic acid (18:2, n-6); about 0-5% stearidonic acid (18:4 n-3); about 0-10% 20:4 n-3, n-5, or n-6; about 0-2% adrenic acid 22:4 n-6; about 0-5% DPAn-3 (22:5); about 10-25% DPAn-6 (22:5); and 0-2% 24:0. In some embodiments, such an oil is from a microorganism of the genus *Schizochytrium*.

An exemplary DHA (triglyceride) containing oil derived from *Schizochytrium* sp. is characterized by the specified amount of components listed in Table 4, where "Max" refers to the amount of the component that can be present up to the specified amount.

TABLE 4

| | CONCENTRATION (WT/WT) |
|---|---|
| FATTY ACIDS | |
| 14:0 | 6.0%-12.0% |
| 16:0 | 18%-28% |
| 18:0 | MAX 2% |
| 18:1 | MAX 8% |
| 18:2 | MAX 2% |
| 20:4 | ARA MAX 2% |
| 20:5 (N-3) EPA | MAX 3% |
| 22:5 (N-6) DPA | 12%-18% |
| 22:6 (N-3) DHA | MIN 35% |
| OTHERS | MAX 10% |
| ELEMENTAL COMPOSITION | |
| ARSENIC | MAX 0.2 PPM |
| COPPER | MAX 0.05 PPM |
| IRON | MAX 0.2 PPM |
| LEAD | MAX 0.1 PPM |
| MERCURY | MAX 0.04 PPM |
| CHEMICAL CHARACTERISTICS | |
| PEROXIDE VALUE | MAX 5 MEQ/KG |
| FREE FATTY ACID | MAX 0.25% |
| MOISTURE AND VOLATILES | MAX 0.05% |
| UNSAPONIFIABLE MATTER | MAX 4.5% |
| TRANS FATTY ACIDS | MAX 1% |

In some embodiments, the DHA-containing compositions can comprise at least about 40 wt % DHA and at least about 0.1 wt % of 4,7,10,13,16,19,22,25 octacosaoctaenoic acid (C28:8). In some embodiments, the compositions comprise at least about 55, 56, 57, 58, 59, 60, 61, 62, 63, 64, 65 wt % DHA, optionally in triglyceride form, as a percentage of total fatty acids. In other embodiments, the compositions comprise at least about 90, 91, 92, 93, 94, 95, 96, 97, 98, or 99 wt % of DHA, optionally in ethyl ester form, as a percentage of total fatty acids. In certain embodiments, the amount of C28:8 in the compositions may be at least about 0.2, 0.3, 0.4, 0.5, 0.6, 0.7, 0.8, 0.9, 1.0, 1.1, 1.2, 1.3, 1.4 or 1.5 wt %. The C28:8 may be present in any form, including triglyceride or ester form. For example, the C28:8 may be present in ethyl ester form. In certain embodiments, the compositions comprise all three of DHA, C28:8 and DPAn-3 in the concentration ranges specified above.

The present invention also provides compositions comprising at least about 40 wt % DHA and at least about 0.1 wt % of DPAn-3. In some embodiments, the compositions comprise at least about 55, 56, 57, 58, 59, 60, 61, 62, 63, 64, 65 wt % DHA, optionally in triglyceride form, as a percentage of total fatty acids. In other embodiments, the compositions comprise at least about 90, 91, 92, 93, 94, 95, 96, 97, 98, or 99 wt % of DHA, optionally in ethyl ester form, as a percentage of total fatty acids. In certain embodiments, the amount of DPAn-3 in the compositions may be at least about 0.1, 0.2, 0.3, 0.4, 0.5, 0.6, 0.7, 0.8, 0.9, or 1.0 wt % of DPAn-3. The DPAn-3 may be present in triglyceride or ester form. For example, the DPAn-3 may be present in ethyl ester form.

In certain embodiments, the compositions comprise all three of the DHA, C28:8 and DPAn-3 in the concentration ranges specified above.

In further embodiments, the compositions may comprise less than about 1.0, 0.9, 0.8, 0.7, 0.6, 0.5, 0.4, 0.3, 0.2, or 0.1 wt % EPA in addition to the DHA and C28:8. In one embodiment, the compositions may comprise less than about 0.25 wt % EPA. The EPA may be present in any form, including triglyceride or ester form. In some embodiments, the compositions may comprise 0 wt % EPA.

The present invention also provides compositions comprising at least about 90 wt % of DHA and at least one additional fatty acid or a derivative thereof. In some embodiments, the amount of DHA in the compositions may be at least about 91, 92, 93, 94, 95, 96, 97, 98, or 99 wt %. In certain embodiments, the additional fatty acid may have a boiling point of about 150-170° C. at a pressure of 0.8 mm Hg.

An exemplary DHA-containing oil derived from the algal oil of *Crypthecodinium Cohnii*, wherein the DHA comprises an ethyl ester, can be characterized by the specified amount of components listed in Table 5, where "Max" refers to the amount of the component that can be present up to the specified amount.

TABLE 5

| DHA CONTENT (MG/G) | 855-945 |
|---|---|
| FATTY ACID CONTENT: % OF TOTAL EE | |
| EICOSAPENTAENOIC ACID (20:5.3) | ND |
| MYRISTIC ACID (14:0) | 0.1% |
| PALMITIC ACID (16:0) | 0.5% |
| PALMITOLEIC ACID (16:1.7) | 0.4% |
| STEARIC ACID (18:0) | ND |
| OLEIC ACID (18:1.9) | 4% |
| LINOLEIC ACID (18:2.6) | ND |
| DOCOSAPENTAENOIC ACID (22:5.3) | 1.3% |
| OCTACOSAOCTAENOIC ACID (28:8.3) | 0.9% |
| TETRACOSAENOIC ACID (24:1.9) | 0.3% |
| OTHERS | 1.1% |

TABLE 5-continued

| DHA CONTENT (MG/G) | 855-945 |
|---|---|
| ELEMENTAL COMPOSITION | |
| ARSENIC | MAX 0.5 PPM |
| COPPER | MAX 0.1 PPM |
| IRON | MAX 0.5 PPM |
| LEAD | MAX 0.2 PPM |
| MERCURY | MAX 0.04 PPM |
| CHEMICAL CHARACTERISTICS | |
| PEROXIDE VALUE | MAX 10.0 MEQ/KG |

ND = NOT DETECTABLE

In some embodiments, an oil is characterized by one or more the following fatty acids (or esters thereof), expressed as wt % of the total fatty acid content. The embodiments provided herein may further comprise about 12% or less, or about 6% to about 12% (wt/wt) of myristic acid (C14-0). The embodiments provided herein may further comprise about 28% or less, or about 18 to about 28% (wt/wt) of palmitic acid (C16:0). The embodiments provided herein may further comprise about 2% or less (wt/wt) of stearic acid (C18:0). The embodiments provided herein may further comprise about 8% or less of (wt/wt) oleic acid (C18:1n-9). The embodiments provided herein may further comprise about 2% or less (wt/wt) of linoleic acid (C18:2). The embodiments provided herein may further comprise about 2% or less (wt/wt) of arachidonic acid (C20:4). The embodiments provided herein may further comprise about 3% or less (wt/wt) of eicosapentaenoic acid (C20:5). The embodiments provided herein may further comprise about 18% or less, or about 12% to about 18% (wt/wt) of decosapentaenoic acid (22:5n-6). The embodiments provided herein may further comprise about 10% or less (wt/wt) of other fatty acids. In some of these embodiments, the ratio of wt % of DHA to wt % of DPAn-6 is about 2.5 to about 2.7. An oil with the preceding characteristics may comprise Life's DHA™ (also formerly referenced as DHA™-S and DHASCO®-S), Martek Biosciences, Columbia, Md.), an oil derived from the Thraustochytrid, Schizochytrium sp., that contains a high amount of DHA and also contains docosapentaenoic acid (n-6) (DPAn-6).

The present invention further includes compositions comprising at least about 70 wt % DHA and at least about 15, 20, or 25 wt % DPAn-6.

Compositions of the present invention also include compositions that comprise at least about 90 wt % of a combination of DPAn-6 and DHA. In certain embodiments, the compositions may comprise at least about 91, 92, 93, 94, 95, 96, 97, 98, or 99 wt % of a combination of DPAn-6 and DHA. In some embodiments, the compositions may comprise at least about 10 wt % DHA and at least about 10 wt % DPAn-6. In other embodiments, the compositions may comprise at least about 15 or 20 wt % DHA and at least about 15 or 20 wt % DPAn-6.

The present invention also provides compositions comprising at least about 90 wt % of a combination of DPAn-6 and DHA, and at least one additional fatty acid or a derivative, such as an ester, thereof. In certain embodiments, the compositions may comprise at least about 91, 92, 93, 94, 95, 96, 97, 98, or 99 wt % of a combination of DPAn-6 and DHA. In some embodiments, the additional fatty acid may have a boiling point of about 150-170° C. at a pressure of 0.8 mm Hg.

The DHA/DPAn-6 compositions described above may further comprise less than about 4% of a saturated fatty acid or an ester thereof. In certain embodiments, the compositions may comprise less than about 3.5%, 3.0%, 2.5%, 2.0%, 1.5%, 1.0% or 0.5% of a saturated fatty acid or a derivative thereof.

The DHA in an oil may be in the form of a DHA ester, preferably an alkyl ester, such as a methyl ester, ethyl ester, propyl ester, or combinations thereof, prepared from an algal oil derived from the Thraustochytrid, Schizochytrium sp. An exemplary DHA (ethyl esters) containing oil derived from Schizochytrium sp. is characterized by the specified amount of components listed in Table 4 of WO 2009/006317, incorporated by reference herein. In some of these embodiments, an oil comprises DHA greater than about 57% (wt/wt), particularly greater than about 70% (wt/wt) of the total fatty acid content of the oil or unit dose. In some of these embodiments, the ratio of wt % of DHA to wt % of DPAn-6 is about 2.5 to about 2.7.

In some embodiments, the composition or oil is characterized by one or more the following fatty acids (or esters thereof, particularly ethyl esters), expressed as wt % of the total fatty acid content. The embodiments provided herein may further comprise about 0.5% or less (wt/wt) of lauric acid (C12:0). The embodiments provided herein may further comprise about 2% or less (wt/wt) of myristic acid (C14:0). The embodiments provided herein may further comprise about 0.5% or less (wt/wt) of myristoleic acid (C14:1). The embodiments provided herein may further comprise about 1% or less of palmitic acid (C16:0). The embodiments provided herein may further comprise about 1% or less (wt/wt) of linoleic acid (C18:2) (n-6). The embodiments provided herein may further comprise about 3% or less (wt/wt) of dihomo gamma linolenic acid (C20:3) (n-6). The embodiments provided herein may further comprise about 0.5% or less (wt/wt) of eicosatrienoic (C20:3) (n-3). The embodiments provided herein may further comprise about 1% or less (wt/wt) of arachidonic acid (C20:4). The embodiments provided herein may further comprise about 3% or less (wt/wt) of eicosapentaenoic acid (C20:5) (n-3). The embodiments provided herein may further comprise about 3% or less (wt/wt) of docosatrienoic acid (22:3). The embodiments provided herein may further comprise about 27% or less (wt/wt) of decosapentaenoic acid (22:5) (n-6). The embodiments provided herein may further comprise about 10% or less (wt/wt) of other components. In some of these embodiments, the ratio of wt % of DHA to wt % of DPAn-6 is about 2.5 to about 2.7. An oil with the preceding characteristics may comprise ethyl ester oil derived from the oil of Thraustochytrid, Schizochytrium sp.

In some embodiments, another exemplary DHA (free fatty acid) containing oil is characterized by the specified amount of components (as ethyl esters) listed in Table 6, where "Max" refers to the amount of the component that can be present up to the specified amount.

TABLE 6

| FATTY ACIDS | CONCENTRATION (WT/WT) |
|---|---|
| C12:0 | MAX 0.5% |
| C14:0 | MAX 2% |
| C14:1 | MAX 0.5% |
| C16:0 | MAX 1% |
| C18:2 N-6 | MAX 1% |
| C20:3 (N-6) | MAX 3% |
| C20:3 (N-3) | MAX 0.5% |
| C20:4 ARA | MAX 1% |
| C20:5 (N-3) EPA | MAX 3% |
| C22:3 | MAX 3% |

TABLE 6-continued

| FATTY ACIDS | CONCENTRATION (WT/WT) |
|---|---|
| C22:5 (N-6) DPA | MAX 27% |
| C22:6 (N-3) DHA | MIN 57% |
| % ADDITIONAL COMPONENTS | MAX 8% |

In some embodiments, another exemplary DHA (free fatty acid) containing oil is characterized by the specified amount of components listed in Table 7:

TABLE 7

| | CONCENTRATION (WT/VT) |
|---|---|
| FATTY ACIDS | |
| 10:0 | MAX 0.5% |
| 12:0 | MAX 0.5% |
| 14:0 | MAX 0.5% |
| 14:1 | MAX 0.5% |
| 16:0 | MAX 0.5% |
| 16:1 | MAX 0.5% |
| 18:1 (N-9) | MAX 0.5% |
| 20:5 (N-3) EPA | MAX 0.5% |
| 22:5 (N-3) DPA | MAX 1% |
| 22:6 (N-3) DHA | MIN 95% |
| 28:8 | MAX 1.5% |
| CHEMICAL CHARACTERISTICS | |
| DOCOSAHEXAENOIC ACID | 946 MG/G |
| DOCOSAHEXAENOIC ACID | 98% |
| FREE FATTY ACIDS | 93% |
| TRANS FATTY ACIDS | <1% |

In some embodiments, the saturated fatty acid or an ester thereof may contain less than 20 carbons, such as, for example, a saturated fatty acid or an ester thereof that contains 19, 18, 17, 16, 15, 14, 13, 12, 11, 10, 9 or 8 carbons. In certain embodiments, the saturated fatty acid or ester thereof may contain 14 or 16 carbons.

In some embodiments, the composition of DHA may further comprise vitamin E. Compounds of the vitamin E group are fat-soluble vitamins with antioxidant properties and includes eight related α-, β-, γ-, and δ-tocopherols and the corresponding four tocotrienols. In some embodiments, the vitamin E in the composition is a tocopherol. In some embodiments, the tocopherol is selected from α-, β-, γ-, and δ-tocopherols, or combinations thereof.

Subject as used herein refers to a human subject at risk for suffering traumatic brain injury. The patient can be at risk, now or at some time in the future, of suffering traumatic brain injury, including mild, moderate and severe forms of closed brain injury or penetrating brain injury.

In the embodiments herein, the compositions of DHA are administered in an amount effective to reduce the risk of pathological effects of traumatic brain injury. As used herein, "reduce the risk of pathological effects" refer to prophylactic therapeutic treatment, wherein the object is to treat or ameliorate the undesired physiological condition or disorder, or obtain beneficial or desired clinical results when the subject is afflicted with the condition or disorder. For purposes herein, beneficial or desired clinical results include, but are not limited to, reducing or alleviating the symptoms associated with traumatic brain injury; diminishment of the extent of the condition associated with traumatic brain injury; reducing or alleviating the condition or disorder of traumatic brain injury, whether detectable or undetectable; or enhancement or improvement of the condition or disorder associated with traumatic brain injury. Prophylactic treatment also includes prolonging survival as compared to expected survival if not receiving treatment.

For the purposes herein, the composition of DHA is administered in a prophylactically effective amount to reduce the risk of suffering pathological effects of traumatic brain injury. As used herein, a "prophylactically effective amount" refers to an amount of DHA effective in achieving a desired therapeutic response in reducing the pathological effects of traumatic brain injury. A prophylactically effective amount of DHA may vary according to factors such as age, sex, and weight of the individual. Administration of a prophylactically effective amount of DHA may be achieved using various regimens, including variations in frequency and time period, sufficient to provide a therapeutic benefit to the subject who suffers traumatic brain injury. In some embodiments, administration of the DHA is daily on consecutive days, or alternatively, the dosage form is administered every other day (bi-daily). Administration may occur on one or more days.

In some embodiments, a prophylactically effective amount of DHA is administered to the subject for a sufficient time period prior to an anticipated engagement in an activity associated with a risk of traumatic brain injury. In some embodiments, a prophylactically effective amount of DHA is administered for at least about 28 days prior to the anticipated engagement in the activity that is associated with a risk of traumatic brain injury. In some embodiments, a prophylactically effective amount of DHA is administered for at least about 6 weeks prior to the anticipated engagement in the activity that is associated with a risk of traumatic brain injury. In some embodiments, a prophylactically effective amount of DHA is administered for at least about two months prior to the anticipated engagement in the activity that is associated with a risk of traumatic brain injury. In some embodiments, a prophylactically effective amount of DHA is administered to the subject for at least about 6 weeks to about 6 months, at least about 2 to about 6 months, or at least about 4 months to about 6 months prior to the anticipated engagement in the activity that is associated with a risk of traumatic brain injury. In some embodiments, a prophylactically effective amount of DHA is administered to the subject for at least about 2 to about 4 months prior to the anticipated engagement in the activity that is associated with a risk of traumatic brain injury.

As used herein, "daily dose," "daily dosage level," "daily dosage amount" or "per day dosage" refer to the total amount of DHA (e.g., in the form of free fatty acids, alkyl esters, or triglycerides) administered per day (about 24 hour period). For example, administration of DHA to a subject at a dose of 2 g per day means that the subject receives a total of 2 g of DHA on a daily basis, whether the DHA is administered as a single dosage form comprising 2 g DHA, or alternatively, four dosage forms comprising 500 mg DHA each (for a total of 2 g DHA). The composition of DHA may be taken in a single application or multiple applications per day. For example, if four capsules are taken daily, each capsule comprising 500 mg DHA, then all four capsules could be taken once per day, or 2 capsules could be taken twice per day, or 1 capsule could be taken every 6 hours. In some embodiments, the composition comprising DHA is administered at least once per day (e.g., single dosage form daily) or at least twice per day (e.g., in two or more dosage forms daily). In some embodiments, the DHA is administered at least two times weekly.

In some embodiments, the DHA is administered in an amount of from about 4 mg/kg body weight/day to about 85 mg/kg body weight/day. In some embodiments, the DHA is administered in an amount of from about 4 mg/kg body weight/day to about 60 mg/kg body weight/day; from about 5 mg/kg body weight/day to about 60 mg/kg body weight/day, from about 10 mg/kg body weight/day to about 60 mg/kg body weight/day, from about 20 mg/kg body weight/day to about 60 mg/kg body weight/day; from about 10 mg/kg body weight/day to about 40 mg/kg body weight/day; or from about 20 mg/kg body weight/day to about 40 mg/kg body weight/day. In some embodiments, the DHA is administered in an amount of about 40 mg/kg body weight/day.

In some embodiments, the DHA is administered in an amount of from about 300 mg to about 6 g per day; from about 0.5 g per day to about 6 g per day; from about 1 g per day to 6 g per day; or from about 2 g per day to 6 g DHA per day. In some embodiments, the DHA is administered in an amount from about 300 mg to about 5 g per day, from about 0.5 g per day to about 5 g per day; from about 1 g per day to about 5 g per day, or from 2 g per day to about 5 g DHA per day. In some embodiments, the DHA is administered in an amount from about 300 mg to about 4 g per day, from about 0.5 g per day to about 4 g per day, from about 1 g per day to about 4 g per day, or from about 2 g per day to about 4 g DHA per day.

In some embodiments, the DHA is administered in an amount of from about 1.5 mg per kg body weight per day to about 125 mg per kg body weight per day. In some embodiments, the DHA is administered in an amount of from about 150 mg to about 10 g per day; from about 0.5 g per day to about 5 g per day; or from about 1 g per day to about 5 g per day.

In some embodiments, the daily amount of DHA administered comprises about 200 mg, 400 mg, 450 mg, 500 mg, 520 mg, 540 mg, 600 mg, 700 mg, 800 mg, 900 mg, 1 g, 1.5 g, 1.8 g, 2.0 g, 2.5 g, 2.7 g, 3.0 g, 3.2 g, 3.3 g, 3.4 g, 3.5 g, 3.6 g, 3.7 g, 3.8 g, 3.9 g, 4.0 g, 4.5 g, 5.0 g, 6.0 g, 6.5 g, 7 g, 8 g, 9 g, or 10 g DHA per day. In some embodiments, the DHA is administered in an amount of at least about 1 g per day.

In some embodiments, the daily dose of DHA administered to a human subject ranges from about 860 mg up to about 6 g, particularly from about 1.7 g up to about 6 g, from about 2.6 g up to about 6 g, particularly from about 3.4 g up to about 6 g, particularly from about 4.3 g to about 6 g and more particularly from about 5.1 g to about 6 g. In some embodiments the daily dose of DHA administered to a human subject ranges from about 860 mg up to about 4 g, particularly from about 1.7 g up to about 4 g, from about 2.6 g up to about 4 g, and more particularly from about 3.4 g up to about 4 g. In some embodiment the daily dose of DHA administered to a human subject ranges from about 860 mg up to about 1 g, particularly from about 860 mg up to about 950 mg. In some embodiments, the daily dose of DHA administered ranges from about 1.7 g up to about 2 g, particularly from about 1.7 g up to about 1.8 g. In some embodiments, the daily dose of DHA administered to a human subject ranges from about 2.6 g up to about 3 g, particularly from about 2.6 g up to about 2.8 g. In some embodiments, the daily dose of DHA administered to a human subject is from about 3.4 g up to about 4 g, particularly from about 3.4 g up to about 3.8 g. In some embodiments, the daily dose of DHA administered to a human subject is from about 4.3 to about 5 g, particularly from 4.3 g to about 4.8 g. In some embodiments, the daily dose of DHA administered to a human subject is from about 5.1 to about 6 g, particularly from about 5.1 to about 5.7 g.

In some embodiments, the daily dose is provided as a unit dose.

In some embodiments, the amount of DHA administered comprises about 300 mg, 400 mg, 450 mg, 500 mg, 520 mg, 540 mg, 600 mg, 700 mg, 800 mg, 900 mg, 1 g, 1.5 g, 1.8 g, 2.0 g, 2.5 g, 3.0 g, 3.5 g, 4.0 g, 5.0 g, or 6.0 g of DHA per day. In some embodiments, the DHA is administered in an amount of about 2 g per day.

In some embodiments, various amounts of DHA may be in a dosage form. In some embodiments, the dosage form comprises less than about 5 g of DHA, about 100 mg to about 3.8 g DHA, about 200 mg to about 3.6 g of DHA, about 500 mg to about 4.0 g DHA, or about 1 g to about 2.0 g DHA. In some embodiments, the dosage form comprises less than about 4 g of DHA, about 200 mg to about 3.9 g DHA, about 500 mg to about 3.7 g of DHA, about 750 mg to about 3.5 g DHA, or about 1 g to about 2 g DHA. In some embodiments, the dosage form of DHA is less than about 3.8 g DHA, about 900 mg to about 3.6 g DHA, or about 1.8 g to about 2.7 g of DHA. In some embodiments, the dosage form of DHA comprises about 200 mg, 400 mg, 450 mg, 500 mg, 900 mg, 1 g, 1.5 g, 1.8 g, 2.0 g, 2.5 g, 2.7 g, 3.0 g, 3.2 g, 3.3 g, 3.4 g, 3.5 g, 3.6 g, 3.7 g, 3.8 g, 3.9 g, 4.0 g, 4.5 g, 5.0 g, 6.0 g, 6.5 g, 7 g, 8 g, 9 g, or 10 g DHA.

Administration of the DHA may be achieved using various regimens. For example, in some embodiments, administration of the DHA is daily on consecutive days, or alternatively, the dosage form is administered every other day (bi-daily). Administration may occur on one or more days. For example, in some embodiments the DHA is administered daily for the duration of the subject's lifetime, or from 1 year to 20 years or 5 years to 10 years. In some embodiments, administration of the DHA dosage form occurs for 7, 14, 21, or 28 days. In some embodiments, the DHA is administered for at least 6 months, for at least 1 yr, for at least 1.5 yrs., for at least 2 yrs., or for at least 5 yrs. In some embodiments, administration of the DHA occurs until a symptom of dementia or AD, e.g., loss of cognitive ability, is halted or reduced, the target being determined by a medical professional.

In some embodiments, the DHA is administered continuously. The term "continuous" or "consecutive," as used herein in reference to "administration," means that the frequency of administration is at least once daily. Note, however, that the frequency of administration can be greater than once daily and still be "continuous" or "consecutive," e.g., twice or even three or four times daily, as long as the dosage levels as specified herein are achieved.

In some embodiments, the amount of DHA administered is an amount that results in maximal amount of DHA in brain phospholipids that is achievable by administration of the DHA containing composition. In some embodiments, the DHA composition is administered to achieve an amount of DHA in the brain phospholipid fraction of at least about 15 wt % of total brain phospholipid. In some embodiments, the DHA composition is administered to achieve an amount of DHA in the brain phospholipid fraction of about 15-22 wt % of total brain phospholipid content. In some embodiments, the DHA composition is administered to achieve an amount of DHA in the brain phospholipid fraction of about 18-20 wt % of total brain phospholipid content. The amount of DHA administered and the duration of administration required to achieve the indicated DHA levels in the brain phospholipid fraction can be determined by those skilled in the art. In some embodiments, the composition comprising DHA is administered to provide a DHA dose of about 2 g per day to 4 g per day to achieve the maximal amount of DHA present in the brain phospholipids.

The effectiveness of the treatment can be assessed using methods generally accepted in the art for determining the severity of traumatic brain injury, such as brain imaging techniques, including computer assisted tomography (CAT) scans, which allow visualization of fractures and evidence of bleeding in the brain (hemorrhage), large blood clots (hematomas), bruised brain tissue (contusions) and brain tissue swelling; and magnetic resonance imaging (MRI), including Susceptibility weighted images (SWI), a sensitive method for detecting small hemorrhages in the brain, and Diffusion tensor imaging (DTI), which consists of a minimum of six scans with diffusion gradients placed in an orthogonal manner. In some embodiments, traumatic brain injury can be assessed by measuring intracranial pressure, which can occur by swelling of the brain.

Since neurobehavioral, particularly cognitive related, problems are a major effect of traumatic brain injury, various methods used to assess cognitive function can be used to assess the effectiveness of prophylactic treatment. Such assessments include, among others, the following. Clinical Dementia Rating Scale (CDR), a dementia staging instrument that classifies cognitive impairment along a continuum from normal aging to mild cognitive impairment to all stages of dementia severity; Folstein Mini-Mental State Exam (MMSE), a commonly used measure of orientation and gross cognitive functioning used by physicians and healthcare providers to screen for cognitive decline; and Alzheimer's Disease Assessment Scale-Cognitive (ADAS-C), a test commonly used in detection of dementia and MCI with repeated measures designs.

Additional methods for assessing cognitive impairment from traumatic brain injury can include, among others, various neuropsychological test, such as the following: Wechsler Test of Adult Reading (WTAR), which is a measure of word pronunciation and is a reliable predictor of pre-morbid general intellectual function; Wechsler Adult Intelligence Scale-3 (WAIS-3)-Kaufman tetrad short form, which is used to measure general intellectual functioning; Repeatable Battery for the Assessment of Neuropsychological Status (RBANS), a comprehensive but relatively rapid, standardized measure of neurocognitive functioning in multiple domains, including memory, attention, language, and visuospatial/constructional functions; Trailmaking Test Part A (Trails A), a widely-used measure of cognitive processing and visuomotor speed, and with Part B, also previously employed in studies of MCI; Trailmaking Test Part B (Trails B), a more complex measure of cognitive processing with executive demands related to mental flexibility and working memory; Controlled Oral Word Association Test (COWAT), a well-known measure of phonemically-controlled verbal fluency, sensitive to cognitive slowing and impairments of executive functioning, which is routinely employed in dementia assessment and MCI studies; Boston Naming Test (BNT), a visual confrontation naming measure utilized to detect anomia or word-finding difficulties, which are common hallmarks of cognitive decline in elderly populations with mild cognitive impairment or early dementia; Automated Neuropsychological Assessment Metrics (ANAM), a computerized test designed to assess several cognitive domains known to be sensitive to change following concussion, including attention and concentration, reaction time, working memory, new learning and memory, and speed of information processing; and SF-36, which measures eight domains of health, including physical functioning, role limitations due to physical health, bodily pain, general health perceptions, vitality, social functioning, role limitations due to emotional problems, and mental health.

In some embodiments, the subject is a human, and as administered a composition comprising DHA as described herein in a range of about 5 mg/kg/day to about 40 mg/kg/day for an extended period of time, e.g., 1 month to 3 months, prior to the traumatic brain injuring event. In some embodiments, the administration of compositions comprising DHA prior to the traumatic brain injuring event mitigates the adverse effects from neuro-inflammation and supports normal brain function following a mild to moderate/severe brain injury, particularly in the absence of penetrating wounds and "excessive" structural damage to the brain. In some embodiments, the administration of compositions comprising DHA prior to the traumatic brain injuring event supports normal energy metabolism in neurons following a brain injury. In some embodiments, the administration of compositions comprising DHA prior to the traumatic brain injuring event maintains and/or improves structural integrity and function of neurons and neuronal axons following mild to moderate brain injury. In some embodiments, the administration of compositions comprising DHA prior to the traumatic brain injuring event supports neuron survival and function following a mild to moderate brain injury. In some embodiments, the administration of compositions comprising DHA prior to the traumatic brain injuring event supports white-matter integrity and optimal (e.g., normal) neurotransmission. In some embodiments, the administration of compositions comprising DHA prior to the traumatic brain injuring event facilitates normal cognitive function post-injury. In some embodiments, the administration of compositions comprising DHA prior to the traumatic brain injuring event support normal memory and learning functions post-injury.

The composition of DHA may be formulated in pharmaceutically acceptable dosage forms. "Pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the compounds (e.g., DHA), compositions, and dosage forms of the present invention are pharmaceutically acceptable. These dosage forms may include, but are not limited to, tablets (including chewable tablets, quick dissolve tablets, effervescent tablets, multi-layer and bi-layer tablets), capsules (including soft and hard gelatin capsules), caplets, cachets, lozenges (including chewable lozenges), beads, pellets, emulsions, liquid, pills, gel caps, elixirs, powders (including reconstitutable powders), granules, and dispersible granules; and parenteral dosage forms which include, but are not limited to, solutions, suspensions, emulsions, particles, microparticles, coated particles, and dry powder comprising an effective amount of the DHA as provided in this disclosure. Various substances are known in the art to coat particles, including cellulose derivatives, e.g., microcrystalline cellulose, methyl cellulose, carboxymethyl cellulose; polyalkylene glycol derivatives, e.g., polyethylene glycol; talc, starch, methacrylates, etc. In some embodiments, the dosage form is a capsule, wherein the capsule is filled with a solution, suspension, or emulsion comprising the DHA. It is also known in the art that the active ingredients may be contained in such formulations with pharmaceutically acceptable excipients such as diluents, fillers, disintegrants, binders, lubricants, surfactants, hydrophobic vehicles, water soluble vehicles, emulsifiers, buffers, humectants, moisturizers, solubilizers, preservatives, flavorants, taste-masking agents, sweeteners, and the like. Suitable excipients may include, e.g., vegetable oils (e.g., corn, soy, safflower, sunflower, or canola oil). In some embodiments, the preservative may be an antioxidant, e.g., sodium sulfite, potassium sulfite, metabisulfite, bisulfites, thiosulfates, thioglycerol, thiosorbitol, cysteine hydrochloride, tocopherol, and combinations thereof. The means and methods for administration are known in the art and an artisan can refer to various pharmacologic references for guidance. For example, "Modern Pharmaceutics," Banker & Rhodes, Informa Healthcare, 4th ed. (2002); and "Goodman & Gilman's The Pharmaceutical Basis o/Therapeutics," McGraw-Hill, New York, 10th ed. (2001) can be consulted.

In some embodiments, specifically excluded from the DHA-containing compositions for administration in the treatment of traumatic brain injury is a complex of DHA and albumin, as described in U.S. Pub. No. 2006/0094654, and Belayev et al., Stroke 36:118-23 (2005), electronically published Nov. 29, 2004.

Administration of DHA may be by oral or parenteral routes (e.g., subcutaneous, intravenous (bolus or infusion), intramuscular, or intraperitoneal). In some embodiments, combinations of different routes of administration can be used. When administered by different routes, the administration can be done concurrently or sequentially. For example, a composition of DHA can be administered orally for chronic administration (e.g., weeks, months before engaging in the activity with risk for traumatic brain injury) and then parenterally to the subject before engaging in an activity with risk for traumatic brain injury. Alternatively, the compositions of DHA can be administered concurrently through different routes, for example parenteral and oral. The dosage forms for these modes of administration may include conventional forms, either as liquid solutions or suspensions, solid forms suitable for solution or suspension in liquid prior to injection, or as emulsions.

In some embodiments, the route of administration is by oral administration. The DHA composition can be administered to subjects in the form of nutritional supplements, foods, pharmaceutical formulations, or beverages, particularly foods, beverages, or nutritional supplements, more particularly, foods and beverages, more particularly foods. A preferred type of food is a medical food (e.g., a food which is in a formulation to be consumed or administered externally under the supervision of a physician and which is intended for the specific dietary management of a disease or condition for which distinctive nutritional requirements, based on recognized scientific principles, are, established by medical evaluation.).

In some embodiments, the dosage form is a pharmaceutical dosage form. "Pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the compounds (e.g., DHA), compositions, and dosage forms of the present invention are pharmaceutically acceptable.

The DHA can be formulated in a dosage form. These dosage forms can include, but are not limited to, tablets, capsules, cachets, pellets, pills, gelatin capsules, powders, and granules; and parenteral dosage forms which include, but are not limited to, solutions, suspensions, emulsions, coated particles, and dry powder comprising an effective amount of the DHA as taught in this invention. In some embodiments, the dosage form can be inserted or mixed into a food substance. Various substances are known in the art to coat particles, including cellulose derivatives, e.g., microcrystalline cellulose, methyl cellulose, carboxymethyl cellulose; polyalkylene glycol derivatives, e.g., polyethylene glycol; talc, starch, methacrylates, etc. In some embodiments, the dosage form is a capsule, wherein the capsule is filled with a solution, suspension, or emulsion comprising the DHA. It is also known in the art that the active ingredients can be contained in such formulations with pharmaceutically acceptable excipients such as diluents, fillers, disintegrants, binders, lubricants, surfactants, hydrophobic vehicles, water soluble vehicles, emulsifiers, buffers, humectants, moisturizers, solubilizers, preservatives, flavorants, taste-masking agents, sweeteners, and the like. Suitable excipients can include, e.g., vegetable oils (e.g., corn, soy, safflower, sunflower, or canola oil). In some embodiments, the preservative can be an antioxidant, e.g., sodium sulfite, potassium sulfite, metabisulfite, bisulfites, thiosulfates, thioglycerol, thiosorbitol, cysteine hydrochloride, .-tocopherol, and combinations thereof. The means and methods for administration are known in the art and an artisan can refer to various pharmacologic references for guidance. For example, "Modern Pharmaceutics," Banker & Rhodes, Informa Healthcare, 4th ed. (2002); "Goodman & Gilman's The Pharmaceutical Basis of Therapeutics," McGraw-Hill, New York, 10th ed. (2001); and Remingtons's Pharmaceutical Sciences, 20th Ed., 2001 can be consulted.

The DHA of the present invention is orally active and this route of administration can be used for the methods described herein. Accordingly, administration forms can include, but are not limited to, tablets, dragees, capsules, caplets, gelatin capsules, and pills, which contain the DHA and one or more suitable pharmaceutically acceptable carriers.

Dosage forms for oral administration may include, but are not limited to, tablets, dragees, capsules, caplets, gel caps, and pills, which contain the DHA and one or more suitable pharmaceutically acceptable carriers. The DHA may be formulated readily by combining these compounds with pharmaceutically acceptable carriers well known in the art. Such carriers enable the compositions of DHA to be formulated as tablets, gel caps, pills, dragees, capsules, liquids, gels, syrups, slurries, suspensions and the like, for oral ingestion by a subject to be treated. In some embodiments, the dosage form is a tablet, gel cap, pill or caplet. Pharmaceutical preparations for oral use may be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl cellulose, sodium carboxymethyl cellulose, vegetable oil (e.g., soybean oil), and polyvinylpyrrolidone (PVP). If desired, disintegrating agents may be added, such as, but not limited to, the cross-linked polyvinyl pyrrolidone, agar, or alginic acid or a salt thereof such as sodium alginate. Pharmaceutical preparations which may be used orally include, but are not limited to, push-fit capsules made of gelatin, as well as soft, sealed capsules made of gelatin (e.g., from porcine or bovine) and a plasticizer, such as glycerol or sorbitol. Capsule shells may be composed of non-animal derived ingredients, i.e., vegetarian ingredients, such as carrageenan, alginate, modified forms of starch, cellulose and/or other polysaccharides. In specific embodiments, the gelatin capsules may be porcine, bovine, vegetarian, or alginate gelatin capsules. All formulations for oral administration should be in dosages suitable for such administration.

In some embodiments, the dosage form is a gel cap having an amount of DHA of about 200 mg to about 2 g, and a pharmaceutically acceptable excipient. In some embodiments, the gel cap has an amount of DHA of about 200 mg, 250 mg, 300 mg, 350 mg, 400 mg, 450 mg, 500 mg, 900 mg, 1 g, 1.5 g, or 2 g, and a pharmaceutically acceptable excipient.

It should be understood that in addition to the ingredients particularly mentioned above, the formulations of this invention can include other suitable agents such as flavoring agents, preservatives, and antioxidants. In particular, it is desirable to mix the microbial oils with an antioxidant to prevent oxidation of the DHA. Such antioxidants are pharmaceutically acceptable and can include vitamin E, carotene, BHT or other antioxidants known to those of skill in the art.

In some embodiments, the dosage form is a nutraceutical dosage form. The term "nutraceutical" refers to any substance that is (1) a sole item of a meal or diet that provides medical and/or health benefits, or (2) a product that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract, or combinations of these ingredients that provides medical and/or health benefits. The medical and/or health benefits can include reducing the risk of a neurological disorder described herein.

In some embodiments, the DHA can be provided in a dietary supplement, medical food or animal feed. "Dietary supplement" refers to a compound or composition used to supplement the diet of an animal or human. In some embodiments, the dietary supplement can further comprise various "dietary ingredients" intended to supplement the diet. "Dietary ingredients" can further include: vitamins, minerals, herbs or other botanicals, amino acids, and substances such as enzymes, organ tissues, glandulars, and metabolites. Dietary ingredients can also include extracts or concentrates. In some embodiments, the dosage form of DHA is administered in a dietary supplement.

The present invention is also directed to use of an oral dosage form consisting essentially of about 430 mg to about 6 g of docosahexaenoic acid (DHA) wherein the dosage form comprises less than about 1% eicosapentaenoic acid (EPA) and less than about 2% docosapentaenoic acid 22:5n-6 (DPAn-6). In some embodiments, the oral dosage form is a unit dosage form, in particular, a gelatin capsule. Optionally the gelatin capsule also comprises a colorant, flavoring, and/or antioxidant.

The present invention is also directed to use of oral dosage forms comprising: (a) about 200 mg to about 4 g of DHA, wherein the DHA is about 40% to about 99.5% (wt/wt) or more of the total fatty acid content of the dosage form; and (b) a pharmaceutically acceptable excipient, wherein the dosage form is substantially free of EPA, and wherein the DHA, such as a DHA alkyl ester, is derived from an algal source.

The present invention includes gelatin capsules that are hard or soft gelatin capsules. In some embodiments, the encapsulating material comprises a gelatin, a plasticizer, and water. In certain embodiments, the encapsulating material is vegetarian, i.e., made from non-animal derived material, including plants, seaweed (for example, carrageenan), food starch, modified corn starch, potato starch, and tapioca. In other embodiments, the encapsulating material is derived from animals, including porcine, bovine, and fish-based materials, such as gelatins. Plasticizers of the invention include glycerin, glycerol, polyols, and mixtures thereof. In some embodiments, the plasticizer is a high boiling point polyol, such as glycerol or sorbitol.

In some embodiments, the gelatin capsule is a soft-gelatin capsule made from gelatin, glycerol, and water, and filled with DHA and an antioxidant. In certain embodiments, the gelatin capsule is animal or vegetable derived. In some embodiments, the gelatin capsule comprises a 0.5 g dosage form, wherein the fill weight of the weight of the dosage form is from about 450 mg to about 550 mg, and wherein the gelatin capsule comprises from about 430 mg to about 480 mg DHA. In some embodiments, the gelatin capsule comprises about 450 mg DHA per 500 mg of the dosage form. In some embodiments, the gelatin capsule comprises about 450 mg DHA per 500 mg of the dosage form. In some embodiments, the gelatin capsule comprises a 1 g dosage form, wherein the fill weight of the dosage form is from about 950 mg to about 1050 mg, and wherein the gelatin capsule comprises from about 860 mg to about 950 mg DHA per 1000 mg of the dosage form. In some embodiments, the gelatin capsule comprises about 900 mg DHA per 1,000 g of the dosage form.

In certain embodiments, the gelatin capsule is vegetarian. In some embodiments, the capsule preparation comprises no animal products, and comprises glycerol (and/or other polyols), seaweed extract (carrageenan) and water. In some embodiments, the water is purified. In some embodiments, color, flavor and/or sweeteners are added. During encapsulation, in some embodiments, fractionated coconut oil is used as a lubricant.

In some embodiments, the gelatin capsule comprises a capsule preparation, an active, and optionally a colorant and/or antioxidant. In another embodiment i) the capsule preparation comprises gelatin (bovine acid hide), glycerin, and purified water, ii) the active comprises DHA-EE, iii) the optional colorant is selected from titanium dioxide, FD&C Yellow #5, FD&C Red 40, and mixtures thereof; and iv) the antioxidant is ascorbyl palmitate. In some embodiments, the raw materials are USP raw materials.

In some embodiments, the gelatin capsules are soft gelatin capsules of about 1 g, having the specifications within the limits set forth in Table 8:

TABLE 8

Specifications for 1 g DHA Ethyl Ester Gelatin Capsules

| TEST | SPECIFICATION |
|---|---|
| DHA EE CONTENT, PER CAPSULE | 855-945 MG |
| AVERAGE FILL WEIGHT | 950-1050 MG |
| DISINTEGRATION | COMPLIES USP |
| ACID VALUE | MAX 2 MG KOH/G |
| PEROXIDE VALUE (PV) | MAX 10 MEQ/KG |
| ANISIDINE VALUE (AV) | MAX 20 |
| MICROBIAL LIMITS TESTS | COMPLIES WITH <61> USP |

Set forth in Table 9 is a list of components that are, in some embodiments, used in the manufacture of a DHA-EE soft gelatin capsule, and at least one corresponding function for each component.

TABLE 9

List of Components in 1 g DHA Ethyl Ester Soft Gelatin Capsules

| COMPONENT | FUNCTION |
|---|---|
| 900 MG DHA EE | ACTIVE |
| GELATIN, BOVINE ACID HIDE | CAPSULE PREPARATION |
| GLYCERIN | CAPSULE PREPARATION |
| PURIFIED WATER | CAPSULE PREPARATION |
| TITANIUM DIOXIDE | COLORANT |
| FD&C YELLOW #5 | COLORANT |
| FD&C RED #40 | COLORANT |

The present invention is also directed to kits or packages comprising one or more dosage forms to be administered according to the methods described herein. A kit or package can contain one dosage form, or more than one dosage form (i.e., multiple dosage forms). If multiple dosage forms are present in the kit or package, the multiple dosage forms can be optionally arranged for sequential administration. The kits can contain dosage forms of a sufficient number to provide convenient administration to a subject who has a chronic condition and requires long-term administration of the DHA of the present invention. For example, in some embodiments, the kit provides dosage forms of a sufficient number for 1, 2, 3 or 4 months of daily administration of the DHA. In some embodiments of the present invention, the kit comprises dosage forms for shorter periods of administration, e.g., the kit can contain about 7, 14, 21, 28 or more dosage forms for oral administration, each dosage form comprising about 450 mg to about 12.05 g DHA and intended for ingestion on successive days.

The kits can optionally contain instructions associated with the dosage forms of the kits. Such instructions can be in a form prescribed by a governmental agency regulating the manufacture, use or sale of pharmaceutical products, which notice reflects approval by the agency of the manufacture, use or sale for human administration to treat a condition or disorder. The instructions can be in any form which conveys information on the use of the dosage forms in the kit according to the methods described herein. By way of example and not limitation, the instructions can be in the form of printed matter, or in the form of a pre-recorded media device.

In the course of examination of a subject, a medical professional can determine that administration of DHA pursuant to one of the methods described herein is appropriate for the subject, or the physician can determine that the subject's condition can be improved by the administration of DHA pursuant to one of the methods described herein. Prior to prescribing any DHA regimen, the physician can counsel the subject, for example, on the various risks and benefits associated with the regimen. The subject can be provided full disclosure of all the known and suspected risks associated with the regimen. Such counseling can be provided verbally, as well as in written form. In some embodiments, the physician can provide the subject with literature materials on the regimen, such as product information, educational materials, and the like.

The present invention is also directed to methods of educating consumers about the methods of treating neurological disorders, the method comprising distributing the DHA dosage forms with consumer information at a point of sale. In some embodiments, the distribution will occur at a point of sale having a pharmacist or healthcare provider.

The term "consumer information" can include, but is not limited to, an English language text, non-English language text, visual image, chart, telephone recording, website, and access to a live customer service representative. In some embodiments, consumer information will provide directions for use of the DHA unit dosages according to the methods described herein, appropriate age, use, indication, contraindications, appropriate dosing, warnings, telephone number, and website address. In some embodiments, the method further comprises providing professional information to relevant persons in a position to answer consumer questions regarding use of the disclosed regimens according to the methods described herein. The term "professional information" includes, but is not limited to, information concerning the regimen when administered according to the methods of the present invention that is designed to enable a medical professional to answer customer questions.

A "medical professional," includes, for example, a physician, physician assistant, nurse practitioner, pharmacist and customer service representative. All of the various aspects, embodiments and options described herein can be combined in any and all variations.

In some embodiments, the DHA is administered in a single dosage form, i.e., a dosage form, or in two or more dosage forms. As used herein, "dosage form" refers to the physical form for the route of administration. The term "dosage form" can refer to any traditionally used or medically accepted administrative forms, such as oral administrative forms, intravenous administrative forms, or intraperitoneal administrative forms. In some embodiments, the DHA is administered in a single dose, i.e., a unit dose. As used herein, a "unit dose" refers to an amount of DHA administered to a subject in a single dose, e.g., in a gel capsule. The term "unit dose" can also refer to a single unit of pharmaceutically suitable solid, liquid, syrup, beverage, or food item, that is administered within a short period of time, e.g., within about 1 minute, 2 minutes, 3 minutes, 5 minutes, 10 minutes, 20 minutes, or 30 minutes.

In some embodiments, the subject to be treated can be administered at least one unit dose per day. In some embodiments, the dosage forms can be taken in a single application or multiple applications per day. For example, if four capsules are taken daily, each capsule comprising about 500 mg DHA, then all four capsules could be taken once daily, or 2 capsules could be taken twice daily, or 1 capsule could be taken every 6 hours. Various amounts of DHA can be in a unit dose. In some embodiments, the unit dose comprises about 430 mg, about 450 mg, about 500 mg, about 550 mg, about 600 mg, about 650 mg, about 700 mg, about 750 mg, about 800 mg, about 850 mg, about 900 mg, about 950 mg, about 1 g, or about 1.5 g, DHA.

In some embodiments, the dosage form has a total weight of about 0.2 g to about 2 g. By way of example and not limitation, a capsule can contain a total weight an algal oil of about 0.2 g, where the algal oil contain comprises DHA at a certain wt % of the total fatty acid content of the algal oil. In some embodiments, the dosage form has a total weight of about 0.2 g, about 0.25, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g or about 1.05 g.

EXAMPLES

Various features and embodiments of the disclosure are illustrated in the following representative examples, which are intended to be illustrative, and not limiting.

Effect of Pretreatment with DHA on Traumatic Brain Injury

Experimental Design.

Two groups of 20 (n=40) of adult male Sprague-Dawley rats were subjected to an impact acceleration injury (IAI) resulting in reproducible severe traumatic brain injury. Rats weighing between 350 and 400 g received induction anesthesia followed by endrotracheal intubation and maintained on inhaled anesthetic using a modified medical anesthesia machine. The animals were then shaved and prepared in sterile fashion surgery, followed by subcutaneous injection of local anesthetic into the planned incision site. A 3 cm midline incision in the scalp was made, periosteal membranes were separated, exposing bregma and lambda. A metal disk 10 mm in diameter and 3 mm thick was attached to the skull with cyanoacrylate and centered between bregma and lambda. The animal were placed prone on a foam bed with the metal disk directly under a Plexiglas tube. A 450 g brass weight was dropped through the tube from a height of 2 meters striking the disk. The animal was then ventilated on 100% $O_2$ while the skull was inspected and the incision repaired. When the animal recovered spontaneous respirations, the endotracheal tube was removed and the animal returned to the cage for postoperative observation (Foda and Marmarou, *J Neurosurg* 80:301-313 (1994)). All procedures involving live animals have been previously reviewed and approved by the Institutional Animal Care and Use Committee of West Virginia University, and were performed according to the principles of the Guide for the Care and Use of Laboratory animals, published by the Institute of Laboratory Resources, National Research Council (NIH publication 85-23-2985).

Animals and Dietary Treatments.

The two treatment groups were housed in the small animal vivarium under veterinary staff supervision for 40 days. At weaning age (21 days) pre-injury, the groups received daily a control diet or that same diet supplemented with algae derived DHA. Each group received rat chow ad lib.

After 28 days on the diets, treatment groups underwent IAI procedure. Following IAI, all dietary groups were fed the control diet (standard chow diet, without added DHA).

Immunohistochemical analyses. Following 7 days post-injury survival, half of the animals in each group were euthanized with a lethal dose injection of 00.5 ml Ketamine and 0.5 ml Xylazine. The animals were immediately perfused transcardially with 200 ml cold 0.9% saline to wash out all blood. This was followed by 4% paraformaldehyde in Millonigs buffer for 40 minutes. The entire brain, brainstem, and rostral spinal cord were removed and immediately placed in 4% paraformaldehyde for 24 hours. Following fixation, the brain was blocked by cutting the brainstem above the pons, cutting the cerebellar peduncies, and then making sagittal cuts lateral to the pyramids. The resulting tissue containing the corticospinal tracts and the medial lemnisci, areas shown previously to yield traumatically injured axons, was then sagitally cut on a vibratome into 40 micron sections. The tissue then underwent temperature controlled microwave antigen retrieval using previously described techniques (Stone et al., *Acta Neuropathol* 97:335-345 (1999)). Briefly, the tissue was preincubated in a solution containing 10% normal goat serum (NGS) and 0.2% triton X in PBS for 40 minutes.

The tissue was incubated in polyclonal antibody raised in rabbit against beta amyloid precursor protein (B-APP) at a dilution of 1:200 in 1% NGS in PBS, then incubated in a secondary anti-rabbit IgG antibody conjugated with Alexa 488 fluorophore for two hours. The tissue underwent a final wash in 0.1M phosphate buffer and then was mounted using an antifade agent and coverslip. The slides were sealed with acrylic and stored in the dark in a laboratory refrigerator (Mills et al., *J Biomed Opt* 8:347-356 (2003)). A similar histological approach was used to assess microglia/macrophage recruitment into the injured brain regions, neuron and oligodendrocyte survival (Huang et al., *Brain* 130:3004-3019 (2007)).

The tissue was then examined and images acquired using a laser scanning confocal microscope system and a 40× objective lens. Ten digital images are obtained from the tissue of each animal, and images are then randomized. Individual injured axons are independently counted and data is stored in an Excel spreadsheet, Statistical analysis of the data is performed using Statistical software.

Behavioral assessment. Fourteen days post-injury, functional evaluation of learning and memory was performed on all four groups. This consisted of pre- and post-injury testing using a Morris Watermaze task (Stone et al., *Acta Neuropathol* 97:335-345 (1999)). Fatty acid blood testing was done prior to the injury and at the end of study.

Animals (rats) were given 0, 3, 9, 40 mg/kg/day of DHASCO oil containing DHA for 28 days prior to inducing traumatic brain injury. Results of the study are shown in Table 10 below.

TABLE 10

|  | Sham | None | 3 mg/kg | 9 mg/kg | 40 mg/kg |
|---|---|---|---|---|---|
| Axon damage(%) | 2 | 100 | 75 | 64 | 15 |
| Neuronal death (%) | 13 | 100 | 73 | 77 | 22 |
| Inflammation | 10 | 100 | 74 | 71 | 31 |
| Water maze navigation (sec) | 22 | 110 | 100 | 94 | 32 |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method for reducing the risk of pathological effects of traumatic brain injury, comprising:
   (a) administering to a subject who is at risk of traumatic brain injury a composition comprising 40-50 wt % docosahexaenoate (DHA) of the total fatty acid content, wherein the composition is administered prior to engagement in an activity associated with a risk of traumatic brain injury to reduce the risk of pathological effects of traumatic brain injury, wherein the composition has an eicosapentaenoate (EPA) content of less than 3 wt % of the total fatty acid content and a docosapentaenoic acid n-6 (DPA n-6) content of 12-18 wt % of the total fatty acid content, and wherein the subject at risk for traumatic brain injury is an athlete participating in a sport with occurrence of concussions.

2. A method for reducing the risk of pathological effects of traumatic brain injury, comprising:
   (a) selecting a subject who is at risk of traumatic brain injury, wherein the subject at risk for traumatic brain injury is an athlete participating in a sport with occurrence of concussions; and
   (b) administering to the subject a composition comprising 40-50 wt % docosahexaenoate (DHA) of the total fatty acid content, wherein the composition is administered in a prophylactically effective amount prior to engagement in an activity associated with a risk of traumatic brain injury to reduce the risk of pathological effects of traumatic brain injury, and wherein the composition has an eicosapentaenoate (EPA) content of about 3 wt % of the total fatty acid content and a docosapentaenoic acid n-6 (DPA n-6) content of 12-18 wt % of the total fatty acid content.

3. The method of claim 1 or 2 in which the DHA is in the form of an alkylester.

4. The method of claim 3 in which the DHA alkylester is a methyl, ethyl or propyl ester.

5. The method of claim 1 or 2 in which the DHA to EPA ratio is at least 10:1.

6. The method of claim 1 or 2 in which the DHA is obtained from a microbial oil.

7. The method of claim 6 in which the microbial oil is an algal oil.

8. The method of claim 6 in which the microbial oil is from *Crypthecodinium cohnii*.

9. The method of claim 6 in which the microbial oil is from *Schizochytrium* sp.

10. The method of claim 1 or 2 in which the traumatic brain injury is a closed head injury.

11. The method of claim 1 or 2 in which the composition is administered for at least 28 days prior to engaging in the activity associated with the risk of traumatic brain injury.

12. The method of claim 1 or 2 in which the composition is administered for at least 6 weeks prior to engaging in the activity associated with a risk of traumatic brain injury.

13. The method of claim 1 or 2 in which the effective amount is a dose of about 10 mg/kg body weight/day to about 40 mg/kg body weight/day of DHA.

14. The method of claim 1 or 2 in which the composition is an oral dosage form.

15. The method of claim 14 in which the oral dosage form is a gelatin capsule.

16. The method of claim 15 in which the gelatin capsule comprises from about 200 mg to about 1 g of DHA, and a pharmaceutically acceptable excipient.

\* \* \* \* \*